US008518999B2

(12) United States Patent
Sneddon et al.

(10) Patent No.: US 8,518,999 B2
(45) Date of Patent: *Aug. 27, 2013

(54) MODULATORS OF TNF-αSIGNALING

(75) Inventors: Scott F. Sneddon, Salem, MA (US);
John L. Kane, Maynard, MA (US);
Bradford H. Hirth, Littleton, MA (US);
Fred Vinick, Lexington, MA (US);
Shuang Qiao, San Diego, CA (US);
Sharon R. Nahill, Belmont, MA (US);
John M. Williams, Hopkinton, MA
(US); Hans-Peter Biemann, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 933 days.

This patent is subject to a terminal disclaimer.

(21) Appl. No.: 11/292,325

(22) Filed: Dec. 1, 2005

(65) Prior Publication Data

US 2006/0173010 A1    Aug. 3, 2006

Related U.S. Application Data

(60) Continuation of application No. 10/797,244, filed on Mar. 10, 2004, now Pat. No. 7,034,031, which is a division of application No. 09/852,965, filed on May 10, 2001, now Pat. No. 6,969,728.

(60) Provisional application No. 60/203,784, filed on May 12, 2000, provisional application No. 60/205,213, filed on May 18, 2000.

(51) Int. Cl.
| | |
|---|---|
| *A61K 31/16* | (2006.01) |
| *A61K 31/4174* | (2006.01) |
| *A61K 31/436* | (2006.01) |
| *A61K 31/395* | (2006.01) |
| *A61K 45/06* | (2006.01) |
| *A61P 37/06* | (2006.01) |
| *C07C 233/00* | (2006.01) |
| *C07D 233/54* | (2006.01) |

(52) U.S. Cl.
USPC ........ 514/612; 514/613; 514/333; 548/336.1; 564/152; 564/155; 564/159

(58) Field of Classification Search
USPC .......................................... 514/612, 613, 333
See application file for complete search history.

(56) References Cited

U.S. PATENT DOCUMENTS

| | | | |
|---|---|---|---|
| 3,935,263 A | 1/1976 | Lestina et al. | |
| 4,303,673 A | 12/1981 | Biedermann et al. | |
| 4,944,796 A | 7/1990 | Wee | |
| 4,997,950 A | 3/1991 | Murphy et al. | |
| 5,540,931 A | 7/1996 | Hewitt et al. | |
| 5,654,312 A | 8/1997 | Andrulis, Jr. et al. | |
| 5,795,967 A | 8/1998 | Aggarwal et al. | |
| 5,801,193 A | 9/1998 | Ojo-Amaize et al. | |

(Continued)

FOREIGN PATENT DOCUMENTS

| | | |
|---|---|---|
| BR | 9606788 A | 12/1997 |
| BR | 9606778 A | 1/1998 |
| CA | 996119 | 8/1976 |
| CA | 2072551 | 12/1992 |
| CA | 2211181 | 8/1996 |
| DE | 2937698 A1 | 4/1981 |
| DE | 3813886 | 11/1989 |
| DE | 3928605 A1 | 3/1991 |
| EP | 0 246 749 A2 | 11/1987 |
| EP | 0 330 959 A2 | 9/1989 |

(Continued)

OTHER PUBLICATIONS

Graninger et al. Curr. Opin. Rhematol. 13(3) 209-13, 2001.*

(Continued)

*Primary Examiner* — Venkataraman Balasubramanian
(74) *Attorney, Agent, or Firm* — Hamilton, Brook, Smith & Reynolds, P.C.

(57) ABSTRACT

The present invention provides compounds which are modulators of TNF-α signaling and methods of use thereof for treating a patient having a TNF-α mediated condition. The compounds can be represented by the following structural formulas:

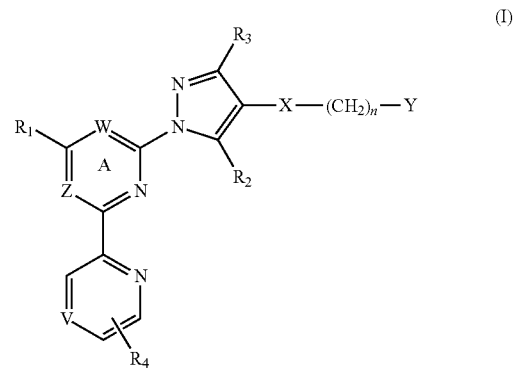

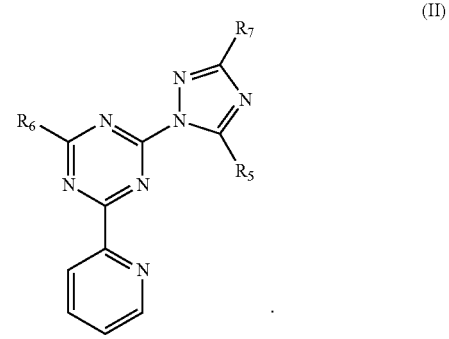

16 Claims, No Drawings

(56) References Cited

U.S. PATENT DOCUMENTS

| | | | |
|---|---|---|---|
| 5,932,737 A | 8/1999 | Itoh et al. |
| 5,958,413 A | 9/1999 | Anagnostopulos et al. |
| 5,990,103 A | 11/1999 | Schonharting et al. |
| 6,020,323 A | 2/2000 | Cohen et al. |
| 6,030,615 A | 2/2000 | Bucala et al. |
| 6,048,841 A | 4/2000 | Baxter et al. |
| 6,204,245 B1 | 3/2001 | Siegel et al. |
| 6,211,160 B1 | 4/2001 | Wilson et al. |
| 6,235,281 B1 | 5/2001 | Stenzel et al. |
| 6,270,766 B1 | 8/2001 | Feldman et al. |
| 6,294,170 B1 | 9/2001 | Boone et al. |
| 6,299,878 B1 | 10/2001 | Pierpaoli et al. |
| 6,306,820 B1 | 10/2001 | Bendele et al. |
| 6,306,840 B1 | 10/2001 | Adams et al. |
| 6,331,560 B1 | 12/2001 | Shohami et al. |
| 6,337,325 B1 | 1/2002 | Schonharting et al. |
| 6,359,061 B1 | 3/2002 | Swayze et al. |
| 6,376,538 B1 | 4/2002 | Adams et al. |
| 6,376,665 B1 | 4/2002 | Duan et al. |
| 6,407,218 B1 | 6/2002 | Tamarkin et al. |
| 6,420,374 B1 | 7/2002 | Bianco et al. |
| 6,432,962 B2 | 8/2002 | Horneman |
| 6,432,968 B1 | 8/2002 | Schonharting et al. |
| 6,503,184 B1 | 1/2003 | Ni et al. |
| 6,506,569 B1 | 1/2003 | Ni et al. |
| 6,509,015 B1 | 1/2003 | Salfeld et al. |
| 6,969,728 B2 | 11/2005 | Sneddon et al. |
| 7,034,031 B2 | 4/2006 | Sneddon et al. |
| 7,217,718 B2 | 5/2007 | Williams |
| 7,678,822 B2 | 3/2010 | Williams |
| 7,687,530 B2 | 3/2010 | Williams |
| 2002/0119988 A1 | 8/2002 | Sneddon et al. |
| 2003/0004091 A1 | 1/2003 | Perricaudet et al. |
| 2004/0072728 A1 | 4/2004 | Fawwaz |
| 2004/0163654 A1 | 8/2004 | Williams |
| 2010/0233158 A1 | 9/2010 | Williams |
| 2010/0256211 A1 | 10/2010 | Williams et al. |

FOREIGN PATENT DOCUMENTS

| | | |
|---|---|---|
| EP | 0 372 326 A2 | 6/1990 |
| EP | 0 401 747 A | 12/1990 |
| GB | 2058752 | 4/1981 |
| JP | 3-73158 | 3/1991 |
| JP | 4036245 (A) | 2/1992 |
| JP | 2001508450 | 6/2001 |
| JP | 2002-520262 | 7/2002 |
| WO | WO 92/17456 | 10/1992 |
| WO | WO 93/17009 | 9/1993 |
| WO | WO 94/08619 | 4/1994 |
| WO | WO 95/09652 | 4/1995 |
| WO | WO 96/32495 | 10/1996 |
| WO | WO 96/35714 | 11/1996 |
| WO | WO 97/19075 A1 | 5/1997 |
| WO | WO 98/30241 | 7/1998 |
| WO | WO 98/39026 | 9/1998 |
| WO | WO 99/00363 | 1/1999 |
| WO | WO 99/06562 | 2/1999 |
| WO | WO 95/12610 | 5/1999 |
| WO | WO 99/28301 | 6/1999 |
| WO | WO 99/50246 | 10/1999 |
| WO | WO 00/26209 | 5/2000 |
| WO | WO 01/00576 A1 | 1/2001 |
| WO | WO 01/34649 | 5/2001 |
| WO | WO 01/42192 A2 | 6/2001 |
| WO | WO 01/81298 A2 | 11/2001 |
| WO | WO 01/87849 | 11/2001 |
| WO | WO 2004/047825 A1 | 6/2004 |
| WO | WO 2004/047826 A1 | 6/2004 |

OTHER PUBLICATIONS

Shaw et al. Expert Opin. Investig. Drugs 9(7) 1469-1478, 2000.*

Waki, et aL"Peptide Synthesis Using the Four-Component Condensation (Ugi Reaction),"*J Am Chem Soc.*, 99(18)6075-6082 (1977).

Tanaka, et a/. "Analytical Studies on Mepirizole and its Metabolites. II. Identification of the Human Urinary Metabolites or Mepirizole with Stable Isotope Labeling," *Chem and Pharm Bul.*, 24(4) 804-807 (1976).

Milata, et al. "2,4,6-Tris(Azol-1-YL)-1,3,5-Triazines: A New Class of Multidentate Ligands," *Heterocycles*, 55(5) 905-924 (2001).

Tanaka, et al. "Analytical Studies on Mepirizole and Its Metabolites. III. Gas Chromatographic Determination of Mepirizole and Its Metabolites in Biological Fluids," *Chem and Pharm Bul.*, 24(4) 808-812 (1976).

Bayer, et al., "Preparation and Properties of Mesoionic Oxazolones," *Chem. Ber.*, 103(8):2581-2597 (1970). CA 73:77105, 1970. Article and Abstract.

Hazebroucq, G., "2, 3, 4, 5 - Tetrahydro-1H-3-benzazepin-1 -ones and hexahydroimidazoisoquinolines," *Ann. Chim* (Paris) 1(5/6):221-254 (1966) CA 66:2461, 1966. Article and Abstract.

Graninger, et al., "One-year inhibition of tumor necrosis factor-$\alpha$: A major success or a larger puzzle?," *Curr. Opin. Rhematol.* 13(3):209-213 (2001).

Shaw, et al., "Metalloproteinase inhibitors: new opportunities for the treatment of rheumatoid arthritis and osteoarthritis," *Expert Opin. Investig.* Drugs 9(7):1469-1478 (2000).

Wrobel, Jay et al., "Syntheses of Tolrestat Analogues containing Additional Substituents in the Ring and Their Evaluation as Aldose Reductase Inhibitors. Identification of Potent, Orally Active 2-Fluoro Derivatives," *J. Med. Chem.* 34:2504-2520 (1991).

Garcia, Jordi at al., "New Synthetic "Tricks". Triphenylphosphine-Mediated Amide Formation From Carboxylic Acids and Azides," *Tetrahedron Letters*, 25(4):4841-4844 (1984).

Coutts, R.T. et al., "Acetylation and pentafluorobenzoylation of lidocaine metabolites in aqueous solution and identification of derivatives by combined gas chromatography/mass spectrometry," *Biomed. Environ. Mss Specrom.* 14(4):173-82 (1987). (From *Chem. Abstracts*, (1987) 107(5), Abstract No. 32462W).

Kondo, Kazumi et aL, "Preparation of amides as vasopressin antagonists, oxytocin antagonists, and vasopressin agonists," Ohtsuka Pharmaceutical Co., Ltd.) Apr. 19, 1989. (From *Chem. Abstracts*, (1999) 130(11), Abstract No. 139333g).

AU2 \ Davis, Peter W. et al., "Automated Solid-Phase Synthesis of Linear Nitrogen-Linked Compounds," an Biotechnology and Bioengineering (Combinatorial Chemistry), 19-28 , Winter 2000.

Barth, et al., "Immunosuppressive Effects of Antilymphocyte Serum in Complement-Deficient Mice: Evidence that Immune Cytolysis is Not Essential for Als Activity", *The Journal of Immunology*, 104(3): 522-524 (Feb. 1970).

Chalasani, Geetha, et al., "The Allograft Defines the Type of Rejection (Acute versus Chronic) in the Face of an Established Effector Immune Response," *The Journal of Immunology*, 172: 7813-7820 (2004).

Couriel, D., et al., "TNF-Alpha Inhibition for the Treatment of Chronic GVHD," Blood, 100(11):847a (2002) Abstract.

Goodman, J. and Mohanakumar T., "Chronic rejection: failure of immune regulation," Front. BioSci., Sep 1;8:s838-44 (2003).

Hancock, W.W., et al., "Costimulatory function and expression of CD40 ligand, CD80, and CD86 n. vascularized murine cardiac allograft rejection," Proc. Natl. Acad. Sci. USA 93:13967-13972 (1996).

Heidenreich, S., et al., "Monocyte Activation for Enhanced Tumour Necrosis Factor-a and Interleukin 6 Production During Chronic Renal Allograft Rejection," *Transplant Immunology*, 2:35-40 (1994).

Hutchinson, I.V., Ph.D., Retrieved from internet, www4.od.nih.gov/biomarkers/b9.htm, Cytokine Gene Polymorphisms, pp. 4 and 5, Jul. 31, 2007.

Jamieson, N. V. et al., "Graft-Versus-Host Disease in Solid Organ Transplantation," *Transplant Int.* 4:67-71 (1991).

Japanese Office Action, Japanese Patent Application No. 2004-555563, mailing date Jun. 21, 2010 (2478.2018-005 Japan).

Japanese Office Action, Japanese Patent Application No. 2004-555618, mailing date Jun. 22, 2010 (2478.2017-005 Japan).

Kunkel, et al., "The Role of TNF in Diverse Pathological Processes," *Biotherapy*, 3: 135-141 (1991).

"Minor Histocompatibility Antigens in GVHD & Graft Rejection," NIH Guide 26(24) (Jul. 1997), 7 pgs.

Notification of Transmittal of the International Search Report or the Declaration, International Application No. PCT/US03/37318, Date of mailing Mar. 30, 2004.

Retrieved from internet, www4.od.nih.gov/biomarkers/b9.htm, Cytokine Gene Polymorphisms, pp. 4 and 5, Jul. 31, 2007.

Sviland, L. And Dickinson, A.M., "A Human Skin Explant Model for Predicting GraftVersus-Host Disease Following Bone Marrow Transplantation," *J. Clin. Pathol.* 52:910-913 (1999).

Turner, D. M., et al., "A Genetic Marker of High TNF-αProduction in Heart Transplant Recipients," *Transplantation*, 60(10):1113-1117 (1995).

Yuan, X., et al., "A Novel CD154 monoclonal antibody in acute and chronic rat vascularized cardiac allograft rejection," *Transplantation* 73(11):1736-1742 (2002).

Notification of Transmittal of International Search Report for PCT/US03/037418, Date of Mailing Apr. 23, 2004. (2478.2017-003).

Notification of Transmittal of the International Search Report or the Declaration for International Application No. PCT/US01/15027, Date of mailing Feb. 8, 2002. (2478.1002-004).

Written Opinion for International Application no. PCT/US01/15027, Date of mailing Mar. 26, 2002. (2478.1002-004).

Notification of Transmittal of the International Preliminary Examination Report for International Application No. PCT/US01/15027, Date of mailing Jul. 16, 2002. (2478.1002-004).

Pan, W., et al., "Blood-brain barrier permeability to Ebiratide and TNF in Acute Spinal Cord Injury," Experimental Neurology, 146:367-373 (1997).

DeForrest, J., et al., "Pharmacology of Novel Imidazole Alcohol Inhibitors of Primate Renin," Journal of Hypertension, 7(2):S15-S19 (1989).

Stankova, M., et al., "Application of One-Bead One-Structure Approach to Identification of Nonpeptidic Ligands," Drug Development Research, 33:146-156 (1994).

Shuman, R.T., et al., "Structure-Activity Studies of Enkephalin Tetrapeptides," Pept.: Synth. Publ-Pept.: Synth., Struct., Eunct, Proc. Am Pept. Symp. 7th (1981), Editor(s): Rich, Daniel H., Gross, E.; Publisher: Pierce Chem. Co., pp. 617-620.

Shimura, T., et al., "Blood-Brain Barrier Transport of Ebiratide and Its Uptake by Cerebral Neuronal Cells," *Annals of the New York Academy of Sciences*, 609-611 (1993) (Abstract only).

Azzazi, M., et al., "TNF-alpha in acute cardiac transplant rejectin", *Cytokines Cell. Mol Ther.*, 5(1) (1999) (abstract only).

Thompson, A.G., et al., "Induction of immune tolerance by dendtritic cells: Implications for preventative and therapeutic immunotherapy of autiommune disease", *Immunology and Cell Biology*, 80: 509-519 (2002).

Wu, T., et al., "Rapamycin and T cell costimulatory blockade as post-translplant treatment promote fully MCH-mismatched allogeneic bone marrow engraftment under irradiation-free conditioning therapy", *Bone Marrow Transplantation*, 29: 949-956 (2002).

El-Gamel, A., et al., "Transforming growth factor-I31 and lung allograft fibrosis", *Europoean Journal of Cardio-Thoracic Surgery*, 13 (424-430 (1998).

Sambiase, n. V., et al., CMV and Transplant-Related Coronary Atheroscleriosis: An Immunohistochemical, *In Situ* Hybridization, and Polymerase Chain Reaction *In Situ* Study, Mod Poth, 13(2) 173-179 (2000).

Yamani, M.Y. "Myocardial Ischemic-Fibrotic Injury After Human Heart Transplantation Is Associated With Increased Progression of Vasculopathy, Decreased Cellular Rejection and Poor Long-Term Outcome", *J Am. Coll. Cardiol*, 39: 970-977 (2002).

Barrett, A. G. M., et al., "Phenol Oxidation and Biosynthesis. Part 26.[1] Isoonitriles in the Synthesis of Benzylisoquinoline Derivatives", *JCS, Perkin Trans I: Org. & Bio-Org Chem.*, 3: 652-661 (1979).

Office Action, dated Mar. 29, 2011, for Canadian Application No. 2,408,408.

Brancaccio, "Nuovi Derivati Dell'antergan," *Il Farmaeo, Edizione Scientifica*, 19(2), pp. 149-158 (1964).

Bossio, et al., "Studies on Isocyanides and Related Compounds: A Novel Synthesis of Pyrroles Via Ugi Reaction," *Synthesis*, vol. 8, pp. 765-766 (1994).

Zlotin, et al., Synthesis of Funtional Derivatives of N-Carboxamidomethyl- and N-Phthalimidomethyl-αAmino Acids and Peptides by Reaction of Amides and Nitriles of α-Amino Acids with Formaldehyde and Primary Amides or Phthalimide, 45(6), pp. 1410-1488 (1996).

Bergnes, et al., "Generation of an UGI Library of Phosphate Mimic-Containing Compounds and Identification of Novel Dual Specific Phosphatase Inhibitors," *Bioorg. & Med. Chem. Lett.*, 9(19), pp. 2849-2854 (1999).

Maison, et al., "Multicomponent Synthesis of Novel Amino Acid-Nucleobase Chimeras: a Versatile Approach to PNA-Monomers," *Bioorganic & Medicinal Chemistry*, 8(6), pp. 1343-1360 (2000).

\* cited by examiner

MODULATORS OF TNF-αSIGNALING

RELATED APPLICATIONS

This application is a continuation application of U.S. Ser. No. 10/797,244, filed Mar. 10, 2004, now U.S. Pat. No. 7,034, 031 which is a divisional application of U.S. Ser. No. 09/852, 965, filed May 10, 2001, now U.S. Pat. No. 6,969,728 which claims the benefit of U.S. Provisional Application No. 60/203,784, filed May 12, 2000, and U.S. Provisional Application No. 60/205,213, filed May 18, 2000. The entire teachings of these applications are incorporated herein by reference.

BACKGROUND OF THE INVENTION

The cytokine tumor necrosis factor α ("TNF-α") has a broad spectrum of biological activities. TNF-α is produced by activated macrophages and a variety of other cells, including antigen-stimulated T cells, activated mast cells and activated natural killer cells. TNF-α is initially produced as a transmembrane protein of about 25 kD. A 17 kD fragment of this membrane protein is proteolytically cleaved from the cell membrane and circulates as a 51 kD homotrimer. TNF-α mediated processes proceed via the interaction of this trimeric protein with a receptor protein at the surface of a target cell.

TNF-α plays an important role in coordinating the body's response to infection, and serves as an important mediator of inflammation. For example, TNF-α signaling cells. TNF-α induces increased binding of leukocytes to endothelial cells, resulting in accumulation of leukocytes at sites of infection. TNF-α signaling has also been implicated in inducing the production of interleukin-1 and prostaglandins by macrophages, and is involved in the breakdown of the extracellular matrix, inducing collagenase in synoviocytes, and in bone resorption via osteoclast activation.

TNF-α has certain effects on the growth and metastatic potential of tumors. For example, certain human tumor cell lines are sensitive to TNF-α in vitro and TNF-α activation may precede killing of tumor cells by macrophages.

High levels of TNF-α are generally associated with chronic immune or inflammatory diseases, and are considered a cause of neural and cellular degeneration. At lower levels, however, TNF-α plays an important role in the cell life cycle, cellular response to foreign attack, and maintenance of homeostasis. For this reason, it will be appreciated that the purpose of this invention is not the complete and absolute inhibition of TNF-α, but rather the modulation of the cellular response to TNF-α levels and the treatment of TNF-α mediated conditions, thereby permitting an effective treatment for the chronic immune and inflammatory responses that occur when excess TNF-α is produced.

The production of TNF-α has been implicated in a variety of disease states including but not limited to the following: septic shock; endotoxic shock; cachexia syndromes associated with bacterial infections, such as tuberculosis and meningitis; viral infections, such as AIDS; parasitic infections, such as malaria; neoplastic disease; autoimmune disease, including some forms of arthritis, especially rheumatoid and degenerative forms; and adverse effects associated with treatment for the prevention of graft rejection. Thus, there is a need for agents which can interrupt or modulate the TNF-α signaling process.

SUMMARY OF THE INVENTION

The present invention provides compounds which are modulators of TNF-α signaling and methods of use thereof for treating a patient having a TNF-α mediated condition.

In one embodiment, the invention provides compounds of Formula (I),

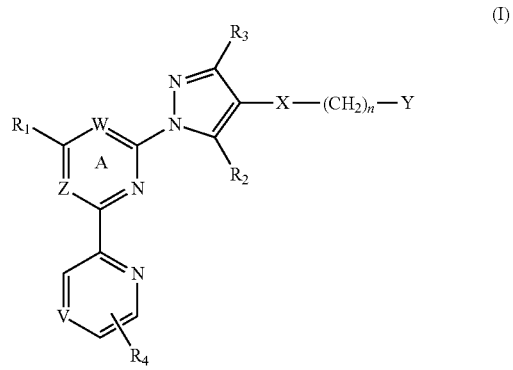

In Formula (I), $R_1$ is H or $NH_2$; $R_2$ and $R_3$ are each, independently, —H, —OH, a substituted or unsubstituted alkyl, or a substituted or unsubstituted alkoxy; $R_4$ is, —H or a substituted or unsubstituted alkyl; X is O, S, $CH_2$ or $SO_2$; V, W and Z are each, independently, N or CH; Y is substituted and unsubstituted phenyl or a substituted and unsubstituted heterocyclyl; and n is 0, 1 or 2.

In another embodiment, the invention provides compounds of Formula II,

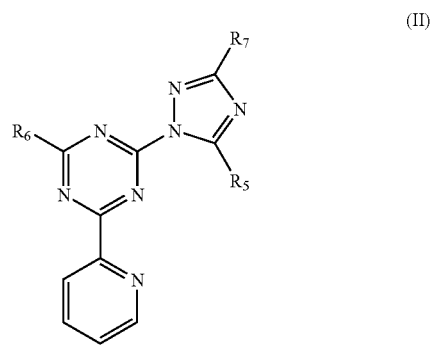

where $R_5$ is substituted or unsubstituted aralkyl, a substituted or unsubstituted cycloalkyl or a substituted or unsubstituted cycloalkylalkyl; $R_6$ is —H or —$NR_{13}R_{14}$; $R_7$ is substituted or unsubstituted phenyl; and $R_{13}$ and $R_{14}$ are each, independently, —H, a substituted or unsubstituted alkyl, a substituted or unsubstituted cycloalkyl, a substituted or unsubstituted aryl, a substituted or unsubstituted aralkyl or $R_{13}$ and $R_{14}$ together with the nitrogen to which they are attached is a heterocycloalkyl.

The present invention further relates to compounds of Formula III,

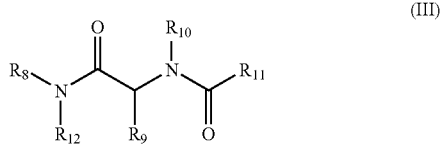

where $R_8$ and $R_{12}$ are each, independently, —H, a substituted or unsubstituted alkyl, a substituted or unsubstituted aryl, a substituted or unsubstituted aralkyl or a substituted or unsubstituted heteroaralkyl; $R_9$ is —H, a substituted or unsubstituted aryl, a substituted or unsubstituted aralkyl, a substituted or unsubstituted heteroaryl or a substituted or unsubstituted heteroaralkyl; $R_{10}$ is substituted or unsubstituted alkyl, a substituted or unsubstituted aryl, a substituted or unsubstituted heteroaralkyl or a substituted or unsubstituted heterocycloalkylalkyl; and $R_{11}$ is substituted or unsubstituted alkyl, a substituted or unsubstituted aryl, a substituted or unsubstituted aralkyl, a substituted or unsubstituted cycloalkylalkyl, a substituted or unsubstituted heteroaryl, a substituted or unsubstituted heteroaralkyl, a substituted or unsubstituted benzophenonyl or a substituted or unsubstituted cycloalkylalkyl.

In yet another embodiment, the present invention relates to a method of treating a TNF-α mediated condition in a patient. The method comprises the step of administering to the patient a therapeutically effective amount of at least one compound of Formula I, Formula II or Formula III, as defined above.

DETAILED DESCRIPTION OF THE INVENTION

The present invention relates to compounds which are antagonists of TNF-α signaling and, therefore, are effective agents for the treatment of TNF-α mediated medical conditions, disorders and diseases, such as chronic inflammation, tissue breakdown and cancer.

For the purposes of the present invention, the language "alkyl" is intended to include a straight chain or branched saturated hydrocarbyl group. Preferred alkyl groups include $C_1$-$C_{12}$-alkyl groups, while more preferred alkyl groups include $C_1$-$C_6$-alkyl groups. The language "cycloalkyl" is intended to include a mono-, bi- or polycyclic alkyl group. Preferred cycloalkyl groups include monocyclic $C_3$-$C_8$-cycloalkyl groups. The language "alkoxy" is intended to include an alkyl-O— group or a cycloalkyl-O— group, where the preferred alkyl and cycloalkyl groups are those given above. The language "aromatic ether" is intended to include an —O-aryl or —O-heteroaryl. The language "alkenyl" is intended to include a straight chain or branched hydrocarbyl group which includes one or more double bonds. Preferred alkenyl groups include $C_2$-$C_{12}$-alkenyl groups. The language "cycloalkenyl" is intended to include a cyclic hydrocarbyl group which includes one or more double bonds but is not aromatic. Preferred cycloalkenyl groups include $C_5$-$C_8$-cycloalkenyl groups.

The language "aryl" is intended to include an aromatic carbocyclic group, such as a phenyl group, a naphthyl group or a phenyl or naphthyl group which is fused with a five or six-membered saturated, partially unsaturated or aromatic carbocyclic ring.

The language "heterocycle" and "heterocyclic group" is intended to include a saturated, aromatic or partially unsaturated ring system which includes at least one heteroatom, such as one or more oxygen, nitrogen or sulfur atoms or a combination thereof.

The language "heterocycloalkyl" is intended to include saturated heterocyclic groups, such as piperidyl, pyrrolidyl, piperazyl, tetrahydrofuranyl and morpholyl.

The language "heteroaryl" is intended to include an aromatic heterocyclic group. Suitable heteroaryl groups include, but are not limited to, pyridyl, pyrimidyl, quinolyl, isoquinolyl, pyrrolyl, quinoxalyl, imidazolyl, oxazolyl, isoxazolyl, pyrazolyl, thienyl, furanyl, pyrazolyl, thiadiazolyl, oxadiazolyl, indazolyl, thiazolyl, isothiazolyl, and tetrazolyl. Heteroaryl groups also include ring systems in which a carbocyclic aromatic ring, carbocyclic non-aromatic ring or heteroaryl ring is fused to one or more other heteroaryl rings, e.g., benzo(b)thienyl, benzimidazolyl, benzoxazolyl, benzothiazolyl, benzothiadiazolyl, benzoxadiazolyl, indolyl, tetrahydroindolyl, azaindolyl, indazolyl, quinolinyl, imidazopyridyl, puryl, pyrrolo[2,3-d]pyrimidyl, pyrazolo[3,4-d]pyrimidyl.

The language "aralkyl" is intended to include an alkyl group which is substituted by one or more aryl groups. A substituted aralkyl can have a substituent on the aryl or on the alkyl portion of the aralkyl. Preferred aralkyl groups include benzyl, diphenylmethyl and 2-phenethyl groups. The language "heteroaralkyl" is intended to include an alkyl group which is substituted by a heteroaryl group or by a heteroaryl group and one or more aryl groups. A substituted heteroaralkyl can have a substituent on the a heteroaryl or on the alkyl portion of the heteroaralkyl. Preferably, a heteroaryl group is an alkyl group substituted by a heteroaryl group.

The language "cycloalkylalkyl" is intended to include an alkyl group substituted with a cycloalkyl group.

The language "heterocycloalkylalkyl" is intended to include an alkyl group substituted with a heterocycloalkyl group.

Alkyl, cycloalkyl, alkenyl, cycloalkenyl, the alkyl portion of an aralkyl, the alkyl portion of a heteroarlkyl, cycloalkylalkyl, and alkoxy groups can be substituted or unsubstituted. Substituted groups of this type can include one or more substituents independently selected from halo, such as fluoro, chloro, bromo and iodo; alkyl, such as $C_1$-$C_6$-alkyl; nitro; hydroxyl; —$NR_{13}R_{14}$, wherein $R_{13}$ and $R_{14}$ are defined as above; —$C(O)R_{15}$, wherein $R_{15}$ is —H, an alkyl, an aryl or an aralkyl; cyano; aryl groups; cycloalkyl groups and heterocyclic groups, such as heteroaryl groups.

Aryl, heterocyclic, such as heteroaryl, aromatic ethers, the aromatic portion of an aralkyl, the aromatic portion of heteroaralkyl, heterocycloalkylalkyl and benzophenone groups can be substituted or unsubstituted. Suitable substituents include one or more substituents independently selected from halo, such as fluoro, chloro, bromo or iodo; alkyl, preferably $C_1$-$C_3$-alkyl; a halogenated alkyl, preferably a halogenated $C_1$-$C_3$-alkyl; alkoxy, preferably $C_1$-$C_3$-alkoxy; aromatic ether; alkyl substituted with an aromatic ether; a hydroxy substituted alkyl; alkoxy substituted aromatic ether; —S-(alkyl); cyano; azide; nitro; —$C(O)R_{15}$; —$NR_{13}R_{14}$; —$C(O)NR_{13}R_{14}$; —$C(O)OR_{16}$, wherein $R_{16}$ is —H, an alkyl, an aryl or an aralkyl; benzyl; 4-(4-benzylpiperazin-1-yl)methyl; 4-4-(2-fluorophenyl)piperazin-1-yl)methyl; a halogenated aryl; methylenedioxo; an aryl; a heteroaralkyl; a heterocycloalkylalkyl; and a heterocyclic, such as a heteroaryl group.

In one embodiment, the present invention provides compounds of Formula I,

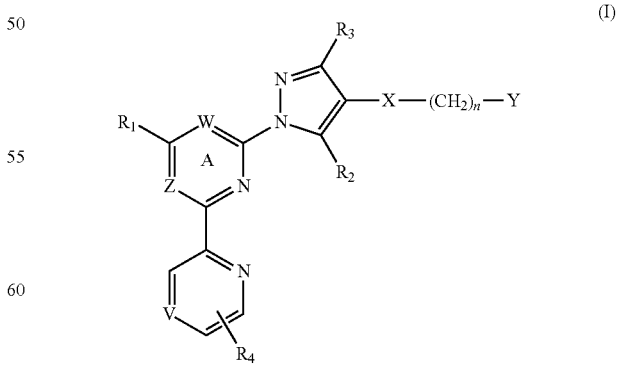

(I)

In Formula (I), $R_1$ is H or $NH_2$; $R_2$ and $R_3$ are each, independently, —H, —OH, a substituted or unsubstituted alkyl or a substituted or unsubstituted alkoxy; $R_4$ is, —H or a substituted or unsubstituted alkyl; X is O, S, $CH_2$ or $SO_2$; V, W and Z are each, independently, N or CH; Y is substituted and unsubstituted phenyl or a substituted and unsubstituted heterocyclyl; and n is 0, 1 or 2.

In one embodiment, Y is a phenyl group which has one or more substituents independently selected from the group consisting of halogen, linear or branched $C_1$-$C_4$-alkoxy, trifluoromethoxy, dioxymethylene, hydroxyalkyl, trifluoromethyl, HC(O)—, linear or branched $C_1$-$C_4$-alkyl, heterocyclyl and substituted or unsubstituted heterocycloalkylalkyl. Preferred substituents for Y include fluoro, chloro, methoxy, morpholyl, N-morpholinomethyl, tetrahydroisoquinolyl, tetrahydroisoquinolinomethyl, 4-(4-benzyl-piperazin-1-yl)methyl, 4-(4-(2-fluoro-phenyl)piperazin-1-yl)methyl and isopropyl. Y can also be a heterocyclyl group, e.g., pyridyl, furyl or pyrrolidyl.

Alternatively in Formula (I), $R_1$-$R_4$, V, W, X, Z and n are as described above, and Y is represented by the following structural formula:

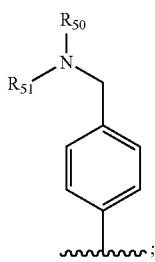

wherein $R_{50}$ and $R_{51}$ are independently an alkyl group, a substituted alkyl group, an aryl group a substituted aryl group, or, taken together with the nitrogen atom to which they are bonded, are a substituted heterocycloalkyl, an unsubstituted heterocycloalkyl, a substituted heteroaryl group or an unsubstituted heteroaryl group. Preferably, $R_{50}$ and $R_{51}$ are, taken together with the nitrogen atom to which they are bonded, an N-substituted piperazyl group, wherein the N-substituent is an aryl group, a substituted aryl group, a —$CH_2$-aryl group or a —$CH_2$-(substituted aryl group), and preferably phenyl, substituted phenyl, benzyl or substituted phenyl. In a preferred embodiment, $R_1$ and $R_4$ are —H, $R_2$-$R_3$ are methyl, V and Z are each —CH—, W is —N—, X is —O— and n is 0. Suitable substituents for a heterocycloalkyl or heteroaryl group formed by $R_{50}$ and $R_{51}$ taken together with the nitrogen atom to which they are bonded are as described below for substituted heterocycles.

In another embodiment, the invention provides compounds of Formula II,

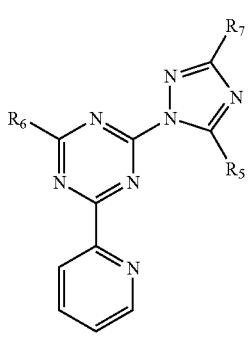

where $R_5$ is substituted or unsubstituted aralkyl, substituted or unsubstituted cycloalkyl or substituted or unsubstituted cycloalkylalkyl; $R_6$ is —H or —$NR_{13}R_{14}$; $R_7$ is substituted or unsubstituted phenyl; and $R_{13}$ and $R_{14}$ are each, independently, —H, a substituted or unsubstituted alkyl, a substituted or unsubstituted cycloalkyl, a substituted or unsubstituted aryl, a substituted or unsubstituted aralkyl or $R_{13}$ and $R_{14}$ together with the nitrogen to which they are attached is a heterocycloalkyl.

In one embodiment, $R_5$ is substituted or unsubstituted benzyl. Suitable substituents on the benzyl group include halogen atoms and linear and branched $C_1$-$C_4$-alkoxy. Preferably, $R_5$ is unsubstituted benzyl or benzyl having one or more substituents independently selected from chloro and methoxy. In another embodiment, $R_5$ is $C_3$-$C_8$-cycloalkyl, $C_3$-$C_8$-cycloalkyl-$C_1$-$C_4$-alkyl or substituted or unsubstituted phenyl-$C_2$-$C_4$-alkyl. For example, $R_5$ can be 2-phenethyl, cyclohexyl or cyclopentylethyl.

$R_7$ is, preferably, phenyl having one or more of the following independently selected substituents: halogen, linear $C_1$-$C_6$-alkyl, branched $C_1$-$C_6$-alkyl, cyclic $C_3$-$C_6$-alkyl or trifluoromethyl. More preferably, $R_7$ is phenyl having one or more of the following independently selected substituents: fluoro, chloro, and linear $C_1$-$C_4$-alkyl or branched $C_1$-$C_4$-alkyl.

The present invention further relates to compounds of Formula III

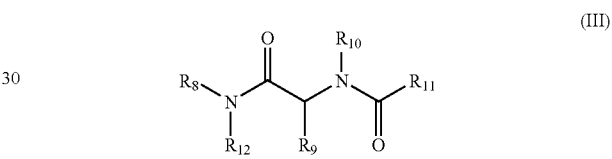

where $R_8$ and $R_{12}$ are each, independently, —H, a substituted or unsubstituted alkyl, a substituted or unsubstituted aryl, substituted or unsubstituted aralkyl or a substituted or unsubstituted heteroaralkyl; $R_9$ is —H, a substituted or unsubstituted aryl, a substituted or unsubstituted aralkyl, a substituted or unsubstituted heteroaryl or a substituted or unsubstituted heteroaralkyl; $R_{10}$ is substituted or unsubstituted alkyl, a substituted or unsubstituted aryl, a substituted or unsubstituted heteroaralkyl or a substituted or unsubstituted heterocycloalkylalkyl; and $R_{11}$ is substituted or unsubstituted alkyl, a substituted or unsubstituted aryl, a substituted or unsubstituted aralkyl, a substituted or unsubstituted cycloalkylalkyl, a substituted or unsubstituted heteroaryl, a substituted or unsubstituted heteroaralkyl, a substituted or unsubstituted benzophenone or a substituted or unsubstituted cycloalkylalkyl.

In a preferred embodiment, one of $R_8$ and $R_{12}$ is —H and the other is substituted or unsubstituted phenyl, phenyl-$C_1$-$C_4$-alkyl, diphenyl-$C_1$-$C_4$-alkyl, linear $C_1$-$C_{12}$-alkyl, branched $C_1$-$C_{12}$-alkyl, cyclic $C_3$-$C_{12}$-alkyl or dicycloalkyl-$C_1$-$C_4$-alkyl. Examples of suitable substituents for the phenyl group(s) of $R_8$ or $R_{12}$ include one or more of the following independently selected groups: alkoxy, such as $C_1$-$C_4$-alkoxy, preferably methoxy; alkyl, such as $C_1$-$C_4$-alkyl, preferably methyl and ethyl; and cyano. Suitable identities for $R_8$ or $R_{12}$ include, but are not limited to, 2,2-diphenylethyl, 2-(4-ethylphenyl)ethyl, benzyl, diphenylmethyl, 1,2-diphenylethyl, 3,3-diphenylpropyl, 3,4,5-trimethoxybenzyl, 2,4,4-trimethylisopentyl, 2-(4-methoxyphenyl)ethyl, 2-cyclopentyl-2-phenylethyl, or 2-phenyl-2-pyridylethyl.

$R_9$ is, preferably, substituted or unsubstituted phenyl, a substituted or unsubstituted phenyl-$C_1$-$C_4$-alkyl, diphenyl-$C_1$-$C_4$-alkyl, phenylfuranyl or heteroaryl-$C_1$-$C_4$-alkyl. Suitable phenyl substituents for a substituted phenyl or a substituted phenyl-$C_1$-$C_4$-alkyl include one or more of the following independently selected groups: cyano; alkyl, such as $C_1$-$C_4$-alkyl, preferably methyl; alkoxy, such as $C_1$-$C_4$-alkoxy, preferably methoxy; $C_1$-$C_4$-alkyl-S—; a halogen, preferably chloro or fluoro; a halogenated $C_1$-$C_4$-alkyl, preferably trifluoromethyl; and phenoxy. A phenoxy substituent can also be substituted with an alkyl or alkoxy group as described above. Suitable identities for $R_9$ include, but are not limited to, phenyl, 2-cyanophenyl, 3-cyanophenyl, 4-cyanophenyl, diphenylmethyl, pyrazolylmethyl, 2,4-dimethylphenyl, 2-methylphenyl, 3-methylphenyl, 4-methylphenyl, 2-methyl-4-methoxyphenyl, 3-methyl-4-methoxyphenyl, 4-methylthiophenyl, 3-chlorophenyl, 3-trifluoromethylphenyl, benzyl, 2-trifluoromethylbenzyl, 3-trifluoromethylbenzyl, 2-chlorobenzyl, 3-chlorobenzyl, 4-chlorobenzyl, 2-methoxybenzyl, 3-methoxybenzyl, 4-methoxybenzyl, 2-fluorobenzyl, 3-fluorobenzyl, 4-fluorobenzyl, 3-azidylphenyl, 3-(4-methoxyphenoxy)phenyl, or 5-phenylfuran-2-yl.

In one embodiment, $R_{10}$ is substituted or unsubstituted phenyl, alkyl substituted with a heteroaryl group, alkyl substituted with a heterocycloalkyl group, or an alkyl substituted with —$NR_{13}R_{14}$, preferably N,N-dialkylamine. Suitable identities for $R_{10}$ include, but are not limited to, 2-(imidazol-4-yl)ethyl, 3-(imidazol-4-yl)propyl, 3-(imidazol-1-yl)propyl 2-(3-methylimidazol-4-yl)ethyl, 2-(morpholin-4-yl)ethyl, 2-(4-pyrazolyl)ethyl, 4-pyrazolylmethyl, 2-N,N-dimethylaminoethyl, 3-N,N-dimethylaminopropyl, and 2-(aminocarbonyl)phenyl.

$R_{11}$ is, preferably, a linear or branched $C_1$-$C_4$-alkyl, substituted or unsubstituted phenyl, substituted or unsubstituted benzophenonyl, pyrazolyl, aminopyrazolyl, substituted or unsubstituted indolyl-$C_1$-$C_4$-alkyl, thiophenyl, quinoxaline, substituted or unsubstituted phenyl-$C_1$-$C_4$-alkyl, pyridylcarbonylphenyl, phenylcarbonyl-$C_1$-$C_4$-alkyl, naphthyl, naphthyl-$C_1$-$C_4$-alkyl, diphenyl-$C_1$-$C_4$-alkyl, $C_5$-$C_8$-cycloalkyl-$C_1$-$C_4$-alkyl, $C_1$-$C_4$-alkylcarbonyl-$C_1$-$C_4$-alkyl, fluorenyl, pryrrolyl, N-methylpyrrolyl, or pyridyl. Suitable substituents on the phenyl ring include halogens, preferably fluoro; furanyl; thiophenyl; phenyl; benzyl; phenoxy; alkyl, such as $C_1$-$C_4$-alkyl, preferably methyl; phenoxyalkyl; $C_1$-$C_4$-alkylcarbonyl; —C(O)-benzyl; and alkoxy, such as $C_1$-$C_4$-alkoxy, preferably methoxy. Suitable substituents on the benzophenonyl ring system include alkoxy, such as $C_1$-$C_4$-alkoxy, preferably methoxy; halogens, preferably chloro; and a $C_1$-$C_4$-alkyl group. Suitable substituents on the indole ring of a indolyl-$C_1$-$C_4$-alkyl include halogens, preferably bromo. Suitable substituents on the $C_1$-$C_4$-alkyl of a phenyl-$C_1$-$C_4$-alkyl include hydroxyl groups. Suitable substituents on the $C_1$-$C_4$-alkyl of a indolyl-$C_1$-$C_4$-alkyl include hydroxyl groups. Suitable identities of $R_{11}$ include, but are not limited to, benzophenon-2-yl, 4'-methoxybenzophenon-2-yl, 4'-chlorobenzophenon-2-yl, 2-(furan-2-yl)phenyl, 2-(thiophen-2-yl)phenyl, 2-benzylphenyl, 2-pyridylcarbonylphenyl, 2-(phenoxymethyl)phenyl, 2-(t-butylcarbonyl) phenyl, 2,2-diphenylethyl, 1-fluorenyl, (naphth-2-yl)methyl, naphth-1-yl, 3-(phenylcarbonyl)propyl, 4-phenylbutyl, 4-butylphenyl, 2-(4-chlorophenylcarbonyl)phenyl, 3-methoxyphenyl, N-methylpyrrol-2-yl, 2,3-dimethoxyphenyl, 3-butyl-2-pyridyl, 2-naphthylmethyl, 2-cyclohexylethyl, 3-methoxyphenyl, N-methyl-2-pyrrolyl, 2-cyclopentylethyl, 3-oxobutyl, 2-benzopyrazyl, quinoxalin-2-yl, 3-idolyl, (2-methylindol-3-yl)methyl, 3-(indol-3-yl)propyl, (indol-3-yl)methyl, (5-bromoindol-3-yl)methyl, 3-chlorophenyl, 3-aminopyrazol-4-yl, 2-(indol-3-yl)-1-hydroxyethyl, 3-fluorophenyl, 1-phenyl-1-hydroxymethyl, 2-phenylphenyl, 2-phenoxyphenyl, thiophen-2-yl, and isopropyl.

Certain compounds of formula I, II or III may contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support, for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I, II or III contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I, II or III and mixtures where the diastereoisomers are unresolved.

Certain compounds of formula I, II or III may exist in different tautomeric forms or as different geometric isomers, and the present invention includes each tautomer and/or geometric isomer of compounds of formula I, II or III and tautomeric mixtures thereof.

Certain compounds of formula I, II or III may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I, II or III and mixtures of conformational isomers thereof.

Certain compounds of formula I, II or III may exist in zwitterionic form and the present invention includes each zwitterionic form of compounds of formula I, II or III and mixtures thereof.

The present invention further relates to pharmaceutically acceptable salts of the compounds of Formulas I, II and III. The phrase a "pharmaceutically acceptable salt" is intended to include a salt which retains the biological effectiveness and properties of the free base and which can be obtained by reaction with an inorganic or organic acid, such as hydrochloric acid, hydrobromic acid, sulfuric acid, nitric acid, phosphoric acid, organic sulfonic acid, organic carboxylic acid, organic phosphoric acid, for example, methanesulfonic acid, ethanesulfonic acid, p-toluenesulfonic acid, salicylic acid, lactic acid, tartaric acid and the like.

Compounds of Formulas I, II and III are modulators of the signaling processes which follow binding of TNF-α to its receptor. In preferred embodiments, the compounds of the invention interrupt the signaling process. Without being bound by theory, it is believed that these compounds interfere with one or more steps of the signaling cascade which includes TNF-α. Thus, these compounds are effective as therapeutic agents for medical conditions in which one or more signaling processes involving TNF-α play a role and include, for example, conditions in which excessive TNF-α is produced. When selecting substituents for the various compounds of Formulas I, II and III, the ordinarily skilled artisan can utilize available information to ensure selection of a stable compound with substituents that will enhance the desired therapeutic activity. The present compounds can be administered to a patient having a TNF-α mediated medical condition, for example, to inhibit the development of the condition, to inhibit its further progression, and/or to ameliorate the symptoms associated with the condition.

Thus, in one embodiment, the present invention relates to a method of treating a TNF-α mediated condition in a patient. The method comprises the step of administering to the patient a therapeutically effective amount of at least one compound of Formula I, Formula II or Formula III, as described above. The patient can be a human or any animal which is suffering from a TNF-α mediated condition or which is believed to be susceptible to development of a TNF-α mediated condition. Preferably, the patient is a domestic animal, such as a fowl, for example, a chicken, or a mammal, for example, a bovine, porcine, canine, feline or equine animal. More preferably, the patient is a human.

The language a "TNF-α mediated condition" is intended to include a medical condition, such as a chronic or acute disease or pathology, or other undesirable physical state, in which a signaling cascade including TNF-α plays a role, whether, for example, in development, progression or maintenance of the condition. Examples of TNF-α mediated conditions include, but are not limited to:

(A) acute and chronic immune and autoimmune pathologies, such as systemic lupus erythematosus (SLE), rheumatoid arthritis, thyroidosis, graft versus host disease, scleroderma, diabetes mellitus, Graves' disease, and the like;

(B) infections, including sepsis syndrome, circulatory collapse and shock resulting from acute or chronic bacterial infection, acute and chronic parasitic infection, and/or infectious diseases, whether bacterial, viral or fungal in origin, such as a HIV or AIDS, and including symptoms of cachexia, autoimmune disorders, Acquired Immune Deficiency Syndrome, dementia complex and infections;

(C) inflammatory diseases, such as chronic inflammatory pathologies, including sarcoidosis, chronic inflammatory bowel disease, ulcerative colitis and Crohn's pathology, and vascular inflammatory pathologies, such as, disseminated intravascular coagulation, atherosclerosis and Kawasaki's pathology;

(D) neurodegenerative diseases, including, demyelinating diseases, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; progressive supranucleo palsy; Cerebellar and Spinocerebellar Disorders, such as astructural lesions of the cerebellum; spinocerebellar degenerations, such as spinal ataxia, Friedreich's ataxia, cerebellar cortical degenerations; multiple systems degenerations, such as Mencel, Dejerine-Thomas, Shi-Drager, and Machado-Joseph; systemic disorders, such as Refsum's disease, abetalipoprotemia, ataxia, telangiectasia, and mitochondrial multisystem disorder; demyelinating core disorders, such as multiple sclerosis, acute transverse myelitis; disorders of the motor unit, such as neurogenic muscular atrophies, such as anterior horn cell degeneration, amyotrophic lateral sclerosis, infantile spinal muscular atrophy and juvenile spinal muscular atrophy; Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, or any subset of conditions, symptoms or syndromes thereof;

(E) malignant pathologies involving TNF-α secreting tumors or other malignancies involving TNF, such as leukemias including acute, chronic myelocytic, chronic lymphocytic and/or myelodyspastic syndrome; lymphomas including Hodgkin's and non-Hodgkin's lymphomas; and malignant lymphomas, such as Burkitt's lymphoma or Mycosis fungoides; and (F) alcohol-induced hepatitis.

See, e.g., Berkow, et al., eds., *The Merck Manual*, $16^{th}$ edition, chapter 11, pp 1380-1529, Merck and Co., Rahway, N. J., (1992), which reference, and references cited therein, are entirely incorporated herein by reference.

The language a "therapeutically effective amount" is intended to include an amount which is sufficient to inhibit, totally or partially, the TNF-α mediated condition, prevent its further progression or ameliorate the symptoms associated with the condition. Such an amount, when administered prophylactically to a patient thought to be susceptible to development of a TNF-α mediated condition, can also be effective to prevent or lessen the severity of the TNF-α mediated condition.

The compounds of this invention can be administered to the patient by themselves or in pharmaceutical compositions where they are mixed with a suitable carrier or excipient at doses to treat or ameliorate the symptoms associated with the TNF-α mediated condition. Mixtures of these compounds can also be administered to the patient as a simple mixture or in suitable formulated pharmaceutical compositions. Techniques for formulation and administration of the compounds of the instant application can be found in *Remington: the Science and Practice of Pharmacy*, $19^{th}$ edition, Mack Publishing Co., Easton, Pa. (1995).

Suitable routes of administration can, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

The compounds of the invention can also be administered in a targeted drug delivery system, such as, for example, in a liposome coated with endothelial cell-specific antibody.

The invention also relates to the use of a compound of Formula I, Formula II or Formula III, as described above, for the manufacture of a medicament for treating a TNF-α mediated condition.

The pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus can be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds can be formulated for parenteral administration by injection, including bolus injection or continuous infusion. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation, for example, subcutaneously or intramuscularly or by intramuscular injection. Thus, for example, the compounds may be formulated with suitable polymeric or hydrophobic materials, for example, as an emulsion in an acceptable oil, or ion exchange resins, or as sparingly soluble derivatives, for example, as a sparingly soluble salt.

The pharmaceutical compositions can also include suitable solid or gel phase carriers or excipients. Examples of such carriers or excipients include calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve the intended purpose. More specifically, a therapeutically effective amount, as previously defined, denotes an amount effective to prevent development of or to alleviate the existing symptoms of the subject being treated. Determination of the effective amounts is well within the capability of those skilled in the relevant art.

For any compound used in the method of the invention, the therapeutically effective dose can be estimated initially from in vitro assays and animal models. For example, a dose can be formulated in cellular and animal models to achieve a circulating concentration range that includes the $IC_{50}$ as determined in cellular assays, i.e., the concentration of the test compound which achieves a half-maximal inhibition of TNF-α activity. In some cases it is appropriate to determine the $IC_{50}$ in the presence of 3 to 5% serum albumin, since such a determination approximates the binding effects of plasma protein on the compound. Such information can be used to more accurately determine useful doses in humans. Further, the most preferred compounds for systemic administration effectively inhibit TNF-α signaling in intact cells at levels that are safely achievable in plasma.

Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl, et al., 1975, in *The Pharmacological Basis of Therapeutics*, Chapter 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the desired effects, or minimal effective concentration (MEC). The MEC will vary for each compound but can be estimated from in vitro data, e.g., the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations. Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will be dependent on the subject being treated, on the subject's weight, the severity of the affliction, the manner of administration and the judgment of the prescribing physician.

Synthetic Strategies

In general, the substituted pyrazole ring of Formula I can be prepared by reaction of a 1,3-dicarbonylalkane with a hydrazine (Scheme I).

Scheme I: Formation of pyrazole ring.

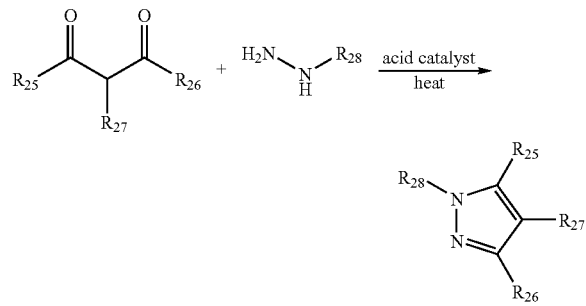

When the method in Scheme I is used to construct the compounds represented by Formula I, $R_{28}$ is ring A and $R_{27}$ is $-X(CH_2)_n-Y$. $R_{25}$ and $R_{26}$ are each, independently, $-H$ or a substituted or unsubstituted alkyl or a substituted or unsubstituted alkoxy. The above reaction was used to prepare the compounds in Examples 6-10 and 12-15.

The reaction to form the pyrazole ring is carried out in a polar solvent, such as water, an alcohol or an ether. Preferably, the reaction is carried out in an alcohol, such as ethanol. The reaction temperature is about 35° C. to about 150° C., preferably about 70° C. to about 90° C. Typically, the reaction is carried out at the reflux temperature of the solvent used.

In compounds which can be represented by Formula I, ring A can be a pyridine, a pyrimidine or a triazine ring. Substituted 2-hydrazinopyrimidines can be prepared by addition of thiourea to 3-(N,N-dimethyamino)prop-2-en-1-one in the presence of a base, followed by in situ methylation of the cyclic thiourea formed (see Scheme II, step 1). The resultant 4-substituted 2-methylsulfanylpyrimidine is treated with hydrazine and heat to form a 4-substituted 2-hydrazinopyrimidines (see Scheme II, step 2).

Scheme II: Preparation of substituted 2-hydrazinopyrimidine.

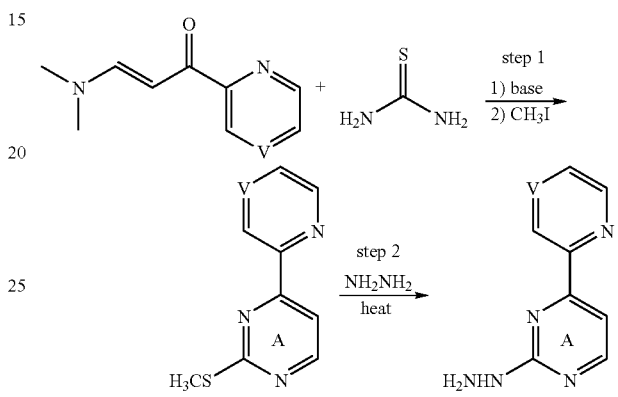

The reaction depicted in Scheme II was used in Example 5 to prepare the intermediate, 2-hydrazino-4-(pyridin-2-yl)-pyrimidine. This intermediate was reacted with a 1,3-dicarbonylalkane via the method shown in Scheme I to prepare a substituted pyrazole in Examples 6-9.

The reaction to form substituted 2-methylsulfanylpyrimidine (see Scheme II, step 1) is carried out in a polar solvent, such as water, an alcohol or an ether. Preferably, the reaction is carried out in an alcohol, such as ethanol, using an alkaline or alkaline earth metal alkoxide as the base. The reaction temperature is about 35° C. to about 150° C., preferably about 70° C. to about 90° C. Typically, the reaction is carried out at the reflux temperature of the solvent used. The reaction is usually allowed to proceed for about 1 hour to about 24 hours, preferably about 2 to about 5 hours at an elevated temperature, then the reaction is cooled and a primary haloalkane, preferably an iodoalkane, is added to alkylate the thiol group.

The substituted 2-methylsulfanylpyrimidine is then treated with hydrazine at elevated temperatures to form substituted 2-hydrazinopyrimidine. The reaction can be carried out in a polar solvent, such as water, an alcohol or an ether. Typically, the reaction is carried out in water having about 35% (vol/vol) hydrazine. The reaction temperature is about 80° C. to about 110° C., preferably, about 100° C.

Substituted 2-hydrazinotriazines can be prepared by reacting 2-amidopyridine or 2-amidoquinoxaline with an alkoxy-bis-(dimethylamino)methane, such as tert-butoxy-bis-(dimethylamino)methane, at a temperature of about 80° C. to about 170° C., preferably at about 145° C. to about 160° C. for about 1 hour to about 5 hours, preferably about 2 hours to about 4 hours to yield a first intermediate. The reaction is typically carried out in a polar aprotic solvent such as dimethylformamide. The 2-amidopyridine or 2-amidoquinoxaline is typically present in a concentration of about 0.2 M to about 1 M and the alkoxy-bis-(dimethylamino)methane is present in about 1.5 equivalents to about 3 equivalents in relation to the 2-amidopyridine or 2-amidoquinoxaline (Scheme III, step 1a).

The first intermediate is then contacted with thiourea and a base in a polar solvent such as water, an alcohol or an ether. Preferably, the reaction is carried out in an alcohol, such as ethanol, using an alkaline or alkaline earth metal alkoxide as the base. The reaction temperature is about 35° C. to about 150° C., preferably about 70° C. to about 90° C. The reaction is usually allowed to proceed for about 1 hour to about 24 hours, preferably about 2 to about 5 hours at an elevated temperature to form a 4-substituted-2-thiotriazine (see Scheme III, step 1b). The 4-substituted-2-thiotriazine is then alkylated and substituted with hydrazine (see Scheme III, steps 2 and 3) to form a substituted 2-hydrazinotriazine via the method described above for forming substituted 2-hydrazinopyrimidine.

Scheme III: Formation of a substituted 2-hydrazinotriazine

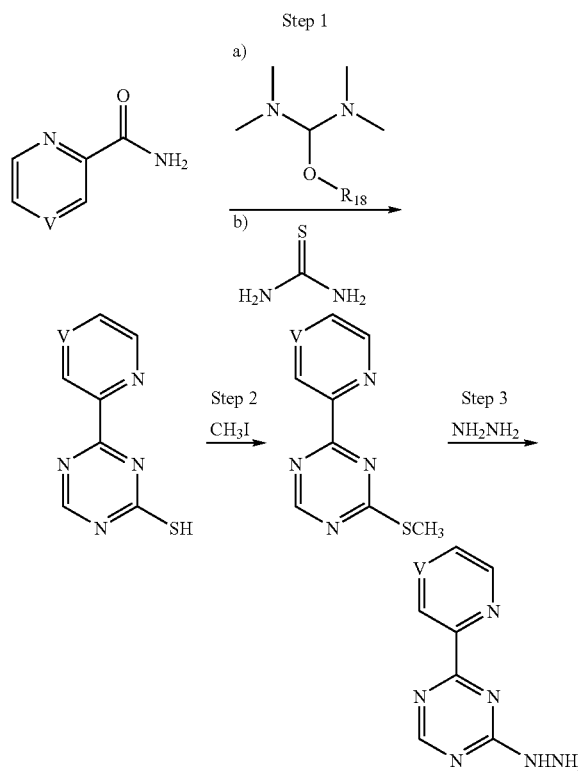

2-Hydrazinotriazine can react with a 1,3-dicarbonylalkane to form a pyrazole ring as shown in the method of Scheme I. Examples 12-14 were prepared via the method of Schemes III followed by the method of Scheme I.

When ring A is a pyridine ring, the pyrazole ring can be formed first by reaction of hydrazine with 1,3-dicarbonylalkane via the method shown in Scheme I where $R_{28}$ is a hydrogen. The pyrazole ring can then be added to the pyridine ring via a substitution reaction (see Scheme IV).

Scheme IV: Formation of a substitute 1-(pyridin-2-yl)pyrazole.

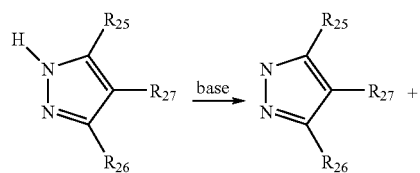

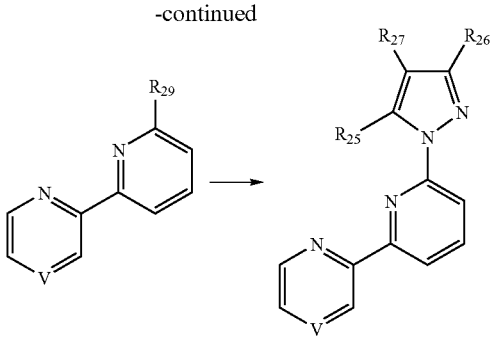

In Scheme IV, $R_{29}$ is a leaving group, such as a halogen. The pyrazole is contacted with a base that is sufficiently strong to deprotonate the pyrazole for about 3 minutes to about 30 minutes prior to addition of the substituted pyridine. Typically, a hydride salt, such as sodium hydride is used. After addition of the substituted pyridine the reaction is heated for about 6 hours to about 24 hours at a temperature of about 80° C. to about 120° C. to form a 6-substituted 2-(pyrazol-1-yl)pyridine. The reaction is typically carried out in an aprotic solvent such as an ether. Example 10 was prepared using the method of Scheme I followed by the method of Scheme IV.

The compounds listed in Tables 2 and 4 were prepared using the methods of Schemes I-IV.

The substituted triazole ring of Formula II can be prepared by reaction of a N-thiocarbonylamide with a hydrazine (see Scheme V).

Scheme V: Formation of a triazole.

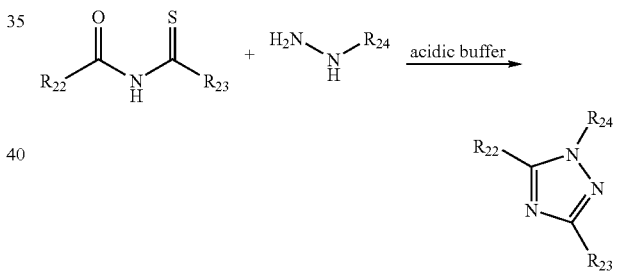

When the reaction in Scheme V is used to form the compounds of Formula II, $R_{24}$ is a 4-(pyridin-2-yl)triazin-2-yl. The reaction is carried out in an acidic buffer, such as carboxylic acid and the salt of the carboxylic acid, for example acetic acid and sodium acetate. An organic solvent can also be present, such as an ether. The reaction is heated to about 70° C. to about 110° C. for about 6 hours to about 24 hours. Example 11 is representative of the method depicted in Scheme V.

The compounds in Table 3 were prepared using the methods of Schemes III and V.

The compounds represented by Formula III can be formed via an Ugi reaction, as shown in Scheme VI.

Scheme VI: Ugi reaction to form the compounds represented by Formula III.

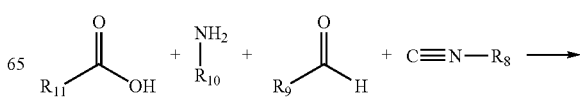

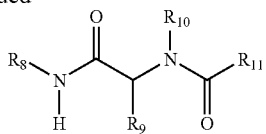

For reviews of Ugi reactions see Gross and Meienhofer, *The Peptides*, vol. 2, pp. 365-381, Academic Press, New York, (1980); *Intra-Sci. Chem. Rep.* (1971), 5:229-261; *Rec. Chem. Prog.* (1969), 30:289-311; and Eberle, et al., *Tetrahedron* (1978), 34:977, the entire teachings of which are incorporated herein by reference. The starting materials for the Ugi reaction, i.e., an isonitrile, a carboxylic acid, an aldehyde or a ketone and an amine, are mixed together in a polar solvent such as an alcohol, preferably methanol or ethanol. The reaction is heated to about 40° C. to about 80° C. for about 6 hours to about 24 hours. Examples 1 and 2 are representative of compounds prepared using an Ugi reaction.

A limitation of the Ugi reaction is that the terminal nitrogen atom, i.e., the nitrogen substituted with $R_8$) is monosubstituted. Therefore, a second method of forming the compounds represented by Formula III was developed wherein the terminal nitrogen can be mono- or disubstituted (see Scheme VII).

equivalents to about 1.5 equivalents, preferably about 1.2 equivalents, of a strong base, such as a hydride salt, for example, sodium hydride, for about 2 minutes to about 20 minutes, followed by addition of about 1.1 equivalents to about 1.5 equivalents, preferably about 1.2 equivalents, of an arylsulfonyl halide or alkylsulfonyl halide. After addition of the arylsulfonyl halide or alkylsulfonyl halide, the reaction is allowed to proceed for about 1 hour to about 6 hours, then about 3 equivalents to about 5 equivalents, preferably about 4 equivalents, of a primary amine is added to the reaction mixture accompanied by addition of a polar solvent such as an alcohol. After addition of the primary amine, the reaction is allowed to proceed for about 6 hours to about 24 hours.

The product of step 2 is treated with about 1.1 equivalents to about 1.8 equivalents of an acid halide in a non-polar solvent, such as a halogenated alkane or an ether in the presence of a base, such as a tertiary amine, for about 1 hour to about 4 hours at a temperature of about 30° C. to about 80° C. to form the desired product. Example 4 is representative of this method.

A third method of forming the compounds represented by Formula III was developed wherein the stereochemistry of the carbon substituted with $R_9$ can be controlled (see Scheme VIII).

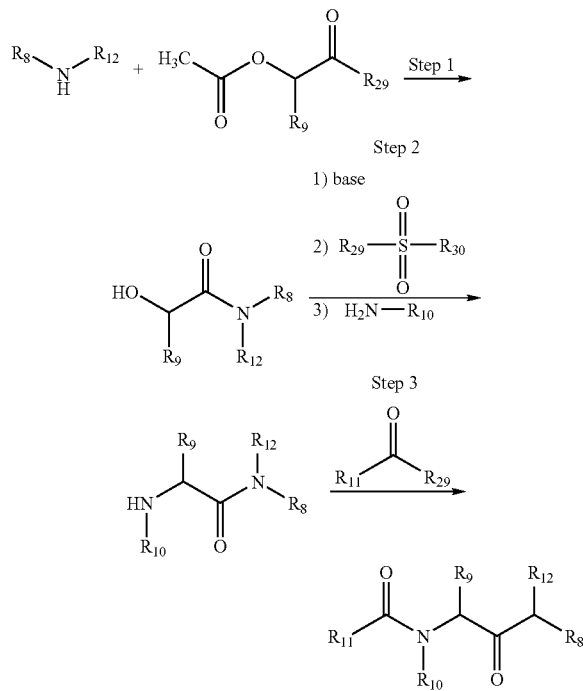

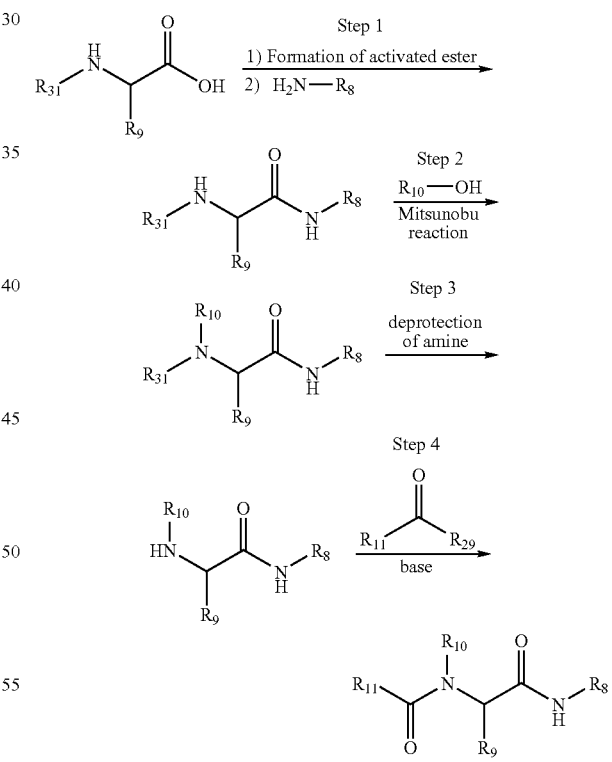

In Scheme VII, $R_{29}$ is a leaving group, such as a halide, and $R_{30}$ is a substituted or unsubstituted aryl or a substituted or unsubstituted alkyl. The starting materials for the first step are mixed together in about equal molar amounts in a nonpolar, aprotic solvent such as methylene chloride, or an ether, for about 0.5 hours to about 6 hours, preferably about 1 hour to form an acetoxyamide. This is followed by hydrolysis with lithium hydroxide to form an α-hydroxyamide.

In step 2, the α-hydroxyamide formed in step I is dissolved in an aprotic solvent, such as an ether, at a concentration of about 0.2 M to about 0.4 M and is treated with about 1.1

In Scheme VIII, $R_{29}$ is a leaving group, such as a halogen and $R_{31}$ is an amine protecting group. Methods for protecting amines can be found in Greene, et al., *Protecting Groups in Organic Synthesis*, 2$^{nd}$ Edition, John Wiley & Sons, Inc., (1991), pp. 309-405, the entire teachings of which are incorporated herein by reference. The starting material for the synthesis depicted in Scheme VIII can be a natural or unnatural amino acid wherein the amine group is protected. Preferred protecting groups for the amine are 9-fluorenylmethyl carbamate and t-butyl carbamate. When a chiral amino acid is the starting material, the chiral center at the α-carbon is retained through out the synthesis.

In step 1 of Scheme VIII, the carboxylic acid of the starting material is transformed into an activated ester by methods known to those skilled in the art. The activated ester is then contacted with a primary amine to form an amide. In step 2, a Mitsunobu reaction is used to displace a hydroxyl group of $R_{10}$—OH with the protected amine of the product formed in step 1 by treating the alcohol with triphenylphosphine and di-tert-butyl azodicarboxylate in the presence of the product of step 1. Fukuyama T., et al., *Tetrahedron Letters* (1995), 36:6373. The amine is then deprotected in step 3 and reacted with an acid halide as described above for step 3 of synthetic Scheme VII. Example 3 is representative of this method.

The compounds of Table I were formed using the methods of Schemes VI-VIII.

EXAMPLES

I. Synthetic Methods

Example 1

2-Benzoyl-N-[(2,2-diphenyl-ethylcarbamoyl)-phenyl-methyl]-N-[2-(1H-imidazol-4-yl)-ethyl]-benzamide (Compound 5)

Step 1) Preparation of 2,2-Diphenylethylisocyanide

A stirred suspension of 2,2-diphenylethylamine (7.00 g, 35.5 mmol) in ethyl formate (25 mL) was heated at reflux overnight. The reaction was concentrated to afford the corresponding formamide as an off-white solid. The crude product was taken up in methylene chloride (50 mL) and diisopropylamine (13.3 mL, 94.9 mmol) and cooled in an ice bath. While stirring, phosphorus oxychloride (5.0 mL, 54 mmol) was added. One hour later, the ice bath was removed and aqueous sodium carbonate solution (75 mL), water (50 mL) and methylene chloride (50 mL) were added. The mixture was stirred vigorously for 1 hour. The organic layer was washed with water, dried (sodium sulfate) and concentrated. The resulting crude product was filtered through a plug of silica (methylene chloride) to afford 6.62 g (90%) of product as an off-white solid: $^1$H NMR (CDCl$_3$) δ 7.38-7.18 (m, 10H), 4.35 (t, J=7.5 Hz, 1H), 3.98 (d, J=7.3, 2H) ppm.

Step 2) Preparation of Compound 5

A solution of histamine (1.11 g, 10.0 mmol), 2-benzoyl-benzoic acid (2.26 g, 10.0 mmol), benzaldehyde (1.06 g, 10.0 mmol) and the product of step 1 (2.07 g, 10.0 mmol) in methanol was heated at reflux overnight. The reaction was concentrated and the residue partitioned between ethyl acetate and aqueous sodium bicarbonate solution. The organic layer was dried (sodium sulfate) and concentrated to afford a foamy light brown solid. Flash chromatography over silica (methylene chloride/methanol) afforded 2.99 g (47%) of the product as a beige solid: $^1$H NMR (CDCl$_3$) δ 7.88-6.84 (m, 25H), 6.65-6.25 (m, 2H), 5.66-5.30 (m, 1H), 4.44-4.20 (m, 1H), 4.17-3.84 (m, 2H), 3.47-3.03 (m, 2H), 2.69-2.18 (m, 2H) ppm. MS (ESI) m/z 634 (M+H$^+$).

Example 2

N-[(4-Cyano-phenyl)-(2,2-diphenyl-ethylcarbamoyl)-methyl]-2-(2,2-dimethyl-propionyl)-N-[2-(1H-imidazol-4-yl)-ethyl]-benzamide (Compound 54)

A solution of histamine (0.100 g, 0.900 mmol), 2-pivaloyl-benzoic acid (0.186 g, 0.902 mmol), 3-cyanobenzaldehyde (0.118 g, 0.900 mmol) and the product of step 1 of example 1 (0.187 g, 0.902 mmol) in methanol was heated at reflux overnight. The reaction was concentrated and the residue partitioned between ethyl acetate and aqueous sodium bicarbonate solution. The organic layer was dried (sodium sulfate) and concentrated to afford 0.521 g (91%) of crude product as an foamy amber solid. This material was used for biological testing without further purification.

Example 3

2-Benzoyl-N-[(1'R)-1'-(2',2'-diphenyl-ethylcarbamoyl)-2'-phenyl-ethyl]-N-[2-(1H-imidazol-4-yl)-ethyl]-benzamide (Compound 47)

Step 1) Preparation of (2R)-2-Amino-N-(2,2-diphenyl-ethyl)-3-phenyl-propionamide To a stirred solution of N-(tert-butoxycarbonyl)-D-phenylalanine (11.0 g, 41.5 mmol) in chloroform (125 mL) was added 1-[3-(dimethylamino)propyl]-3-ethylcarbodiimide hydrochloride (7.95 g, 41.5 mmol) and 1-hydroxybenzotriazole (5.60 g, 41.4 mmol). After 5 minutes, 2,2-diphenylethylamine (7.44 g, 37.7 mmol) was added. The reaction was stirred for 2 hours, diluted with chloroform (100 mL) and washed with aqueous sodium bicarbonate solution. The organic layer was dried (sodium sulfate) and concentrated to afford an off-white solid. Trituration with ether afforded the crude amide. This material was taken up in methylene chloride (100 mL) and treated with trifluoroacetic acid (45 mL, 580 mmol). After stirring for 15 minutes, the reaction was concentrated and the residue was partitioned between ethyl acetate and aqueous sodium bicarbonate. The organic layer was dried (sodium sulfate) and concentrated to afford 12.4 g (111% yield inflated by entrained residual solvent) of product as a colorless gum: $^1$H NMR (CDCl$_3$) δ 7.34-6.95 (m, 15H), 4.10 (t, J=8.2, 1H), 3.88-3.79 (m, 2H), 3.68-3.61 (m, 1H), 3.49 (br s, 2H), 3.13-3.03 (m, 1H), 2.70-2.59 (m, 1H) ppm.

Step 2) Preparation of (2R)—N-(2,2-Diphenyl-ethyl)-2-(2-nitro-benzenesulfonylamino)-3-phenyl-propionamide To a stirred solution of the product of step 1 (12.3 g, 35.6 mmol) in methylene chloride (200 mL) was added 2-nitrobenzenesulfonyl chloride (9.00 g, 40.6 mmol) followed by triethylamine (6.4 mL, 46 mmol). After 30 minutes the reaction was concentrated and the residue partitioned between ethyl acetate and aqueous sodium 5 bicarbonate solution. The organic layer was dried (sodium sulfate) and concentrated. The resulting amber foam was purified by flash chromatography over silica (hexane/ethyl acetate) to afford 14.0 g (74%) of product as a colorless foam: $^1$H NMR (CDCl$_3$) δ 7.95-7.87 (m, 1H), 7.76-7.62 (m, 3H), 7.35-7.15 (m, 10H), 7.06-6.94 (m, 3H), 6.90-6.83 (m, 2H), 6.42 (t, J=5.6, 1H), 5.80 (d, J=5.8, 1H), 4.12 (t, J=8.1, 1H), 4.01-3.82 (m, 3H), 3.18-3.08 (m, 1H), 2.68-3.57 (m, 1H) ppm.

Step 3) Preparation of (2R)—N-(2,2-Diphenyl-ethyl)-2-{(2-nitro-benzenesulfonyl)-[2-(1-trityl-1H-imidazol-4-yl)-ethyl]-amino}-3-phenyl-propionamide To a stirred solution of the product of step 2 (3.40 g, 6.42 mmol) and 2-(1-trityl-1H-imidazol-4-yl)-ethanol (2.73 g, 7.70 mmol) in methylene chloride (40 mL) was added triphenylphosphine (2.19 g, 8.35 mmol) followed by di-tert-butyl azodicarboxylate (1.77 g, 7.69 mmol). After 3 hours the reaction was concentrated and the residue partitioned between ethyl acetate and aqueous sodium bicarbonate solution. The organic layer was dried (sodium sulfate) and concentrated to yield an amber gum. Flash chromatography over silica (methylene chloride/methanol) afforded 5.42 g (97%) of partially purified product (contaminated with di-tert-butyl hydrazodiformate) as a pale yellow foam: $^1$H NMR (CDCl$_3$) δ 7.81-7.74 (m, 1H), 7.64-7.55 (m, 1H), 7.53-7.44 (m, 2H), 7.41-7.03 (m, 31H), 6.69 (t, J=5.6, 1H), 6.53 (s, 1H), 4.48 (t, J=8.1, 1H), 4.08 (t, J=8.1, 1H), 3.84-3.58 (m, 4H), 3.44-3.34 (m, 1H), 2.91-3.80 (m, 1H), 2.78-2.68 (m, 1H), 2.63-2.51 (m, 1H) ppm.

Step 4) Preparation of (2R)—N-(2,2-Diphenyl-ethyl)-3-phenyl-2-[2-(1-trityl-1H-imidazol-4-yl)-ethylamino]-propionamide To a stirred solution of the product of step 3 (5.42 g, 6.26 mmol) in N,N-dimethylformamide (17 mL) was added mercaptoacetic acid (1.1 mL, 15.8 mmol) followed by lithium hydroxide hydrate (1.31 g, 31.2 mmol). The mixture was stirred for 3 hours and then partitioned between ethyl acetate and aqueous sodium bicarbonate solution. The organic layer was combined with a second ethyl acetate extract, dried (sodium sulfate) and concentrated to furnish an amber oil. Flash chromatography over silica (methylene chloride/methanolic ammonia solution) provided 2.50 g (59%) of product as a colorless tacky foam: $^1$H NMR (CDCl$_3$) δ 7.54 (t, J=5.5, 1H), 7.38-7.01 (m, 31H), 6.33 (s, 1H), 4.16 (t, J=8.3, 1H), 4.02-3.92 (m, 1H), 3.83-3.74 (m, 3.22-3.15 (m, 1H), 3.12-3.04 (m, 1H), 2.51-2.18 (m, 5H) ppm.

Step 5) Preparation of 2-Benzoyl-N-[(1'R)-1-(2',2'-diphenyl-ethylcarbamoyl)-2'-phenyl-ethyl]-N-[2-(1-trityl-1H-imidazol-4-yl)-ethyl]-benzamide 2-Benzoylbenzoic acid (1.33 g, 5.88 mmol) was taken up in a 2M solution of oxalyl chloride in methylene chloride (4.5 mL, 9.0 mmol). One drop of N,N-dimethylformamide was added and the frothy mixture was stirred for 2 hours before concentrating. To the residue was added a solution of the product of step 4 (2.50 g, 3.67 mmol) in chloroform (30 mL) and triethylamine (1.05 mL, 7.53 mmol). The mixture was heated at reflux for 2.5 hours. At this time, more triethylamine (0.50 mL, 3.6 mmol) was added and the reaction was heated for additional 30 minutes. The reaction was then concentrated and the residue was partitioned between ethyl acetate and aqueous sodium bicarbonate solution. The organic layer was dried (sodium sulfate) and concentrated to afford an amber foam. This material was filtered through silica (methylene chloride/methanolic ammonia solution) to afford 1.44 g (44%) of a pale amber foam which was used without further purification in the next step.

Step 6) Preparation of Compound 47

A stirred solution of the product of step 5 (1.44 g, 1.62 mmol) in 4:1 acetic acid/water (7 mL) was heated in a water bath (90° C.) for 30 minutes. The reaction solution was then cooled and partitioned between ethyl acetate and aqueous sodium carbonate solution. The organic layer was combined with a second ethyl acetate extract, dried (sodium sulfate) and concentrated to afford an amber foam. Flash chromatography over silica (methylene chloride/methanol) afforded 0.62 g (59%) of product as a foamy pale amber solid. Comparisons by thin layer chromatography and $^1$H NMR spectroscopy indicated that this material is identical to the corresponding racemic Ugi product, compound 43. Analytical chiral HPLC (ChiralPack AD, 4.6×250 mm; eluant: 0.1% diethylamine in 88:12 hexane/ethanol; flow: 1 mL/min; detection: 260 nM) indicated that the material is a single enantiomer within detection limits: $^1$H NMR (CDCl$_3$) δ 8.35 (br s, 1H), 7.90-6.94 (m, 27H), 6.78-6.57 (m, 1H), 6.39-6.17 (m, 1H), 4.65-3.72 (m, 4H), 3.64-2.70 (m, 5H), 2.46-2.18 (m, 1H) ppm. MS (ESI) m/z 648 (M+H$^+$).

Example 4

2-Benzoyl-N-{[(2,2-diphenyl-ethyl)-methyl-carbamoyl]-phenyl-methyl}-N-[2-(1H-imidazol-4-yl)-ethyl]-benzamide (Compound 26)

Step 1) Preparation N-(2,2-Diphenyl-ethyl)-2-hydroxy-N-methyl-2-phenyl-acetamide To a stirred solution of (2,2-diphenylethyl)methylamine (4.97 g, 23.5 mmol) in chloroform (50 mL) was added O-acetylmandelic chloride (5.3 mL, 24 mmol) followed by triethylamine (4.0 mL, 29 mmol). The reaction was stirred for 1 hour and then concentrated. The residue was partitioned between ethyl acetate and aqueous sodium bicarbonate solution. The organic layer was dried (sodium sulfate) and concentrated to afford a colorless gum. The crude amide was taken up in 1:1 tetrahydrofuran/methanol (80 mL) and treated with 1 N aqueous lithium hydroxide (30 mL, 30 mmol). The mixture was stirred for 2 hours and concentrated to remove the organic solvents. The remaining aqueous solution was diluted with water and extracted twice with ethyl acetate and once with methylene chloride. The combined organic extracts were dried sodium sulfate) and concentrated to afford an off-white solid. This material was triturated with diethyl ether to afford 7.59 g (93%) of product as a white solid: $^1$H NMR (CDCl$_3$) δ 7.43-6.98 (m, 15H), 5.07 (s, 1H), 4.57-4.44 (m, 1H), 4.36-4.28 (m, 1H), 3.76-3.64 (m, 1H), 2.46 (s, 3H) ppm.

Step 2) Preparation of N-(2,2-Diphenyl-ethyl)-2-[2-(1H-imidazol-4-yl)-ethylamino]-N-methyl-2-phenyl-acetamide To stirred solution of the product of step 1 (1.50 g, 4.34 mmol) in tetrahydrofuran (15 mL) was added a 60% dispersion of sodium hydride in mineral oil (0.210 g, 5.25 mmol). After gas evolution ceased, p-toluenesulfonyl chloride (0.990 g, 5.20 mmol) was added and the mixture was stirred for 2 hours. At this time, histamine (1.93 g, 17.4 mmol) was added followed by methanol (10 mL). The reaction was stirred overnight and concentrated. The residue was partitioned between ethyl acetate and aqueous sodium carbonate solution. The organic layer was dried (sodium sulfate) and concentrated to afford a pasty white solid. Flash chromatography over silica (methylene chloride/methanolic ammonia solution) provided 1.08 g (57%) of product as a colorless tacky foam: $^1$H NMR (CDCl$_3$) δ 7.52-7.43 (m, 1H), 7.40-7.00 (m, 15H), 6.78-6.69 (m, 1H), 4.36-3.97 (m, 4H), 2.92-2.20 (m, 7H) ppm.

Step 3) Preparation of Compound 26

2-Benzoylbenzoic acid (0.341 g, 1.51 mmol) was taken up in a 2M solution of oxalyl chloride in methylene chloride (1.5 mL, 3.0 mmol). One drop of N,N-dimethylformamide was added and the frothy mixture was stirred overnight and concentrated. A solution of the crude 2-benzoylbenzoyl chloride in methylene chloride (4 mL) followed by triethylamine (0.25 mL, 1.8 mmol) was added to the product of step 2 (0.220 g, 0.502 mmol). The mixture was heated at reflux for 2 hours and concentrated. The residue was taken up in 5:1 methanol/1 N aqueous lithium hydroxide (12 mL) and stirred for 1 hour. The reaction was again concentrated and the residue was partitioned between ethyl acetate and aqueous sodium bicarbonate solution. The organic layer was dried (sodium sulfate) and concentrated to afford a foamy amber solid. Flash chromatography over silica (methylene chloride/methanol) provided 0.229 g (71%) of product as a foamy pale amber solid: $^1$H NMR (CDCl$_3$) δ 7.91-6.92 (m, 26H), 6.54-6.39 (m, 1H), 6.34-6.06 (m, 1H), 4.83-4.31 (m, 2H), 3.97-2.82 (m, 3H), 2.70-2.39 (m, 3H), 2.35-2.09 (m, 2H) ppm. MS (ESI) m/z 648 (M+H$^+$).

Example 5

2-Hydrazino-4-(Pyridin-2-yl)-Pyrimidine

Step 1) Preparation of 2-Methylsulfanyl-4-pyridin-2-yl-pyrimidine. (Synthetic Intermediate Used in Examples 6, 7, 8 & 15)

To a stirred solution of sodium ethoxide (freshly prepared from sodium metal (5.11 g, 222 mmol) and ethanol (350 mL)) was added 3-dimethylamino-1-pyridin-2-yl-propenone (28.0 g, 159 mmol) and thiourea (12.9 g, 170 mmol). The solution was heated to reflux and stirred for 3 hours. The solution was allowed to cool to room temperature, and then iodomethane (13.8 mL, 222 mmol) was added dropwise over 10 minutes. The solution was stirred at room temperature for 2 hours, and then diluted with saturated ammonium chloride solution (250 mL) and water (250 mL). The suspension was extracted with ethyl ether (200 mL×3), and the combined organic extracts washed with saturated sodium thiosulfate solution (150 mL) and brine (150 mL). The organic phase was dried (magnesium sulfate), filtered, and concentrated to provide 30.1 g (96%) of the product as a brown oil: $^1$H NMR (CDCl$_3$) δ 8.70-8.69 (m, 1H), 8.64 (d, J=5.2 Hz, 1H), 8.48 (d, J=7.9 Hz, 1H), 8.01 (d, J=5.2 Hz, 1H), 7.87-7.82 (m, 1H), 7.41-7.38 (m, 1H), 2.65 (s, 3H) ppm $^{13}$C NMR (CDCl$_3$) δ 172.6, 163.1, 158.5, 153.9, 149.7, 137.3, 125.7, 122.0, 112.6, 14.5 ppm.

Step 2) Preparation of (4-Pyridin-2-yl-pyrimindin-2-yl)-hydrazine

To hydrazine hydrate (90 mL) was added 2-methylsulfanyl-4-pyridin-2-yl-pyrimidine (30.0 g, 148 mmol). The solution was heated to reflux and stirred for 17 hours. The solution was allowed to cool to room temperature, and a yellow precipitate formed. The solids were removed by filtration, washed with water, and dried to provide 22.5 g (81%) of the product as yellow micro needles: $^1$H NMR (DMSO-d$_6$) δ 8.68-8.67 (m, 1H), 8.45-8.41 (m, 2H), 8.29 (s, 1H), 7.98-7.93 (m, 1H), 7.52-7.48 (m, 2H), 4.28 (s, 2H) ppm. $^{13}$C NMR (DMSO-d$_6$) δ 164.6, 162.6, 159.3, 153.9, 149.4, 125.5, 121.0, 106.0 ppm.

Example 6

2-[4-(4-Isopropyl-phenoxy)-3,5-dimethyl-pyrazol-1-yl]-4-pyridin-2-yl-pyrimidine (Compound 97)

Step 1) Preparation of 3-(4-Isopropyl-phenoxy)-pentane-2,4-dione

To a refluxing solution of 4-isopropylphenol (0.548 g, 4.02 mmol) and rhodium(II) acetate (ca. 15 mgs) in benzene (10 mL) was added a solution of 3-diazo-pentane-2,4-dione (0.507 g, 4.02 mmol) in benzene (20 mL) over 40 minutes. The reaction mixture was allowed to cool to room temperature and was concentrated to afford a green oil. Flash chromatography over silica (ethyl acetate/hexanes) provided 0.371 g (39%) of the product as a white solid: $^1$H NMR (CDCl$_3$) δ 14.4 (s, 1H), 7.15 (d, J=8.6 Hz, 2H), 6.82 (d, J=8.6 Hz, 2H), 2.87 (sept, J=7.0 Hz, 1H), 2.04, (s, 6H), 1.23 (d, J=7.0 Hz, 6H) ppm.

Step 2) Preparation of Compound 97

To a solution of 3-(4-isopropyl-phenoxy)-pentane-2,4-dione (0.371 g, 1.58 mmol) in ethanol (20 mL) was added (4-pyridin-2-yl-pyrimindin-2-yl)-hydrazine (0.296 g, 1.58 mmol) and p-toluenesulfonic acid monohydrate (ca. 10 mgs). The solution was heated to reflux and stirred for 14 hours. The reaction mixture was allowed to cool to room temperature, diluted with water (100 mL), and extracted with ethyl acetate (100 mL). The organic phase was washed with saturated sodium hydrogencarbonate solution (50 mL) and brine (50 mL), dried (magnesium sulfate), filtered, and concentrated to afford a yellow solid. Flash chromatography over silica (methanol/methylene chloride) provided 0.421 g (69%) of the product as a light yellow solid: $^1$H NMR (CDCl$_3$) δ 8.93 (d, J=5.1 Hz, 1H), 8.75-8.74 (m, 1H), 8.46 (d, J=7.9 Hz, 1H), 8.24 (d, J=5.1 Hz, 7.88 (dt, J=7.9, 1.7 Hz, 1H), 7.46-7.42 (m, 1H), 7.14 (d, J=8.7 Hz, 2H), 6.88 (d, J=8.7 Hz, 2H), 2.88 (sept, J=6.9 Hz, 1H), 2.69 (s, 3H), 2.23 (s, 3H), and 1.23 (d, J=6.9 Hz, 6H) ppm. $^{13}$C NMR (CDCl$_3$) δ 164.3, 160.2, 157.5, 156.4, 153.4, 149.7, 145.4, 142.5, 137.9, 137.2, 133.1, 127.4, 125.7, 122.0, 114.7, 114.0, 33.3, 24.1, 12.7, 11.3 ppm.

Example 7

2-{4-[4-(4-Benzyl-piperazin-1-ylmethyl)-phenoxy]-3,5-dimethyl-pyrazol-1-yl}-4-pyridin-2-yl-pyrimidine (Compound 104)

Step 1) Preparation of {4-[3,5-Dimethyl-1-(4-pyridin-2-yl-pyrimidin-2-yl)-1H-pyrazol-4-yloxy]-phenyl}-methanol To a solution of 3-(4-acetoxymethyl-phenoxy)-pentane-2,4-dione (1.24 g, 4.69 mmol) in ethanol (30 mL) was added (4-pyridin-2-yl-pyrimindin-2-yl)-hydrazine (0.877 g, 4.69 mmol) and p-toluenesulfonic acid monohydrate (about 10 mgs). The reaction mixture was heated to reflux and stirred for 14 hours. The solution was allowed to cool to room temperature, and water (100 mL) was added. The resulting precipitate was removed by filtration, washed with water, and dried to provide a white solid. This crude material was dissolved in 5:1 methanol/water (60 mL) and treated with excess potassium carbonate. The reaction mixture was stirred at room temperature for 2 hours and then diluted with water (100 mL). The precipitate that formed was isolated by filtration, washed with water, and dried to provide 1.53 g (87%) of the product as a white solid. $^1$H NMR analysis was consistent with the assigned structure.

Step 2) Preparation of 4-[3,5-Dimethyl-1-(4-pyridin-2-yl-pyrimidin-2-yl)-1H-pyrazol-4-yloxy]-benzaldehyde To a solution of {4-[3,5-dimethyl-1-(4-pyridin-2-yl-pyrimidin-2-yl)-1H-pyrazol-4-yloxy]-phenyl}-methanol (1.53 g, 4.10 mmol) in chloroform (80 mL) was added the Dess-Martin periodinane (2.36 g, 5.56 mmol). The reaction mixture was stirred at room temperature for 3 hours and then concentrated to provide a white paste. Flash chromatography over silica (methanol/methylene chloride) provided 1.37 g (90%) the product as a white solid. $^1$H NMR analysis was consistent with assigned structure.

Step 3) Preparation of Compound 104

To a solution of 4-[3,5-dimethyl-1-(4-pyridin-2-yl-pyrimidin-2-yl)-1H-pyrazol-4-yloxy]-benzaldehyde (0.545 g, 1.47 mmol) and 1-benzylpiperazine (0.310 g, 1.76 mmol) in dichloroethane (10 mL) was added sodium triacetoxyborohydride (0.436 g, 2.06 mmol). The reaction mixture was stirred at room temperature for 17 hours. The solution was diluted with methylene chloride (50 mL) and washed with saturated sodium hydrogencarbonate (2×30 mL) and brine (50 mL). The organic phase was dried (magnesium sulfate), filtered, and concentrated to afford a yellow oil. Flash chromatography over silica (2 M ammonia in methanol/methylene chloride) provided 0.183 g (23%) of the product as a white foam: $^1$H NMR (CDCl$_3$) δ 8.94-8.93 (m, 1H), 8.75 (d, J=3.9 Hz, 1H), 8.46 (d, J=7.9 Hz, 1H), 8.25 (d, J=3.9 Hz, 1H), 7.90-7.87 (m, 1H), 7.46-7.43 (m, 1H), 7.31-7.21 (m, 7H), 6.89 (d, J=8.5 Hz, 2H), 3.52 (s, 2H), 3.47 (s, 2H), 2.68 (s, 3H), 2.48 (br s, 8H), 2.21 (s, 3H) ppm.

Example 8

2-[4-(4-Chloro-benzylsulfanyl)-3,5-dimethyl-pyrazol-1-yl]-4-pyridin-2-yl-pyrimidine (Compound 119)

Step 1) Preparation of 3-(4-Chloro-benzylsulfanyl)-pentane-2,4-dione

To a solution of 3-chloro-pentan-2,3-dione (1.94 g, 14.4 mmol) in ethylene glycol dimethyl ether (50 mL) was added sodium hydrogencarbonate (ca. 15 g) and 4-chlorobenzyl mercaptan (2.29 g, 14.4 mmol). The suspension was heated to reflux and stirred for 3 hours. The reaction mixture was allowed to cool to room temperature, and water (200 mL) was added. The mixture was extracted with ethyl ether (100 mL×2), and the combined organic extracts washed with brine (150 mL). The organic phase was dried (magnesium sulfate), filtered, and concentrated to afford a yellow oil. Flash chromatography over silica (ethyl acetate/hexanes) provided 2.48 g (67%) of the product as a white solid: $^1$H NMR (CDCl$_3$) δ 7.26 (d, J=8.4 Hz, 2H), 7.06 (d, J=8.4 Hz, 2H), 3.60 (s, 2H), 2.13 (s, 6H) ppm.

Step 2) Preparation of Compound 119

To a solution of 3-(4-chloro-benzylsulfanyl)-pentane-2,4-dione (1.15 g, 4.48 mmol) in ethanol (60 mL) was added (4-pyridin-2-yl-pyrimidin-2-yl)-hydrazine (0.838 g, 4.48 mmol) and p-toluenesulfonic acid monohydrate (ca. 20 mgs).

The solution was heated to reflux and stirred for 5 hours. The reaction mixture was allowed to cool to room temperature, and water (200 mL) was added. The precipitate that formed was isolated by filtration and recrystallized from aqueous methanol to provide 1.36 g (74%) of the product as white needles: $^1$H NMR (CDCl$_3$) δ 8.94-8.92 (m, 1H), 8.75-8.73 (m, 1H), 8.41 (d, J=7.9 Hz, 1H), 8.28-8.26 (m, 1H), 7.91 (t, J=7.9 Hz, 1H), 7.46-7.43 (m, 1H), 7.20 (d, J=8.0 Hz, 2H), 6.89 (d, J=8.0 Hz, 2H), 3.66 (s, 2H), 2.46 (s, 3H), 2.28 (s, 3H) ppm. $^{13}$C NMR (CDCl$_3$) δ 164.6, 160.5, 157.4, 155.2, 153.5, 149.8, 147.3, 137.6, 137.2, 133.1, 130.6, 128.7, 126.1, 122.2, 114.7, 111.3, 40.1, 14.2, 12.6 ppm.

Example 9

2-[4-(4-Chloro-phenylmethanesulfonyl)-3,5-dimethyl-pyrazol-1-yl]-4-pyridin-2-yl-pyrimidine (Compound 124)

To a suspension of 2-[4-(4-chloro-benzylsulfanyl)-3,5-dimethyl-pyrazol-1-yl]-4-pyridin-2-yl-pyrimidine (0.920 g, 2.26 mmol) and sodium hydrogencarbonate (4.10 g, 48.8 mmol) in acetone (125 mL) and water (45 mL) was added Oxone (3.47 g, 5.64 mmol). The reaction mixture was stirred at room temperature for 18 hours. The mixture was treated with excess sodium hydrosulfide, stirred for 15 minutes, and extracted with ethyl acetate (3×50 mL). The combined organic phases were washed with brine (100 mL), dried (magnesium sulfate), filtered, and concentrated to afford a white solid. The crude product was triturated with hot methanol followed by flash chromatography over silica (methanol/methylene chloride) to provide 0.230 g (23%) of the product as a white solid. $^1$H NMR analysis was consistent with assigned structure.

Example 10

6-[4-(4-Chloro-benzylsulfanyl)-3,5-dimethyl-pyrazol-1-yl]-[2,2']bipyridinyl (Compound 126)

Step 1) Preparation of 4-(4-Chloro-benzylsulfanyl)-3,5-dimethyl-1H-pyrazole

To a solution of crude 3-(4-chloro-benzylsulfanyl)-pentane-2,4-dione [prepared as described above from 3-chloropentan-2,3-dione (1.03 g, 7.63 mmol) and 4-chlorobenzyl mercaptan (1.21 g, 7.63 mmol)] in ethanol (60 mL) was added hydrazine hydrate (0.713 mL, 22.9 mmol) and p-toluenesulfonic acid monohydrate (ca. 25 mg).

The solution was heated to reflux and stirred for 15 hours. The reaction mixture was allowed to cool to room temperature, and water (300 mL) was added. The precipitate that formed was removed by filtration, washed with water, and dried to provide 1.38 g (72%) of the product as a white solid: $^1$H NMR (CDCl$_3$) δ 7.17 (d, J=8.4 Hz, 2H), 6.92 (d, J=8.4 Hz, 2H), 3.57 (s, 2H), and 2.02 (s, 6H) ppm. $^{13}$C NMR (CDCl$_3$) δ 137.2, 132.7, 130.3, 128.3, 105.2, 39.9, 10.7 ppm.

Step 2) Preparation of Compound 126

To a solution of 4-(4-chloro-benzylsulfanyl)-3,5-dimethyl-1H-pyrazole (0.708 g, 2.80 mmol) in 2-methoxyethyl ether (7 mL) was added sodium hydride (0.123 g (60% dispersion), 3.08 mmol). After stirring for 5 minutes, 6-bromo-[2,2']bipyridinyl (0.691 g, 2.94 mmol) was added, and the reaction mixture was heated to 100° C. for 16 hours. The reaction mixture was allowed to cool to room temperature, and water (100 mL) was added. The suspension was extracted with ethyl acetate (50 mL×2), and the combined organic extracts washed with brine (100 mL). The organic phase was dried (magnesium sulfate), filtered, and concentrated to afford a tan solid. Flash chromatography over silica (methanol/methylene chloride) followed by recrystallization from aqueous methanol provided 0.485 g (43%) of the product as a white solid: $^1$H NMR (CDCl$_3$) δ 8.70-8.68 (m, 1H), 8.34 (d, J=7.9 Hz, 1H), 8.29 (d, J=7.9 Hz, 1H), 7.94 (t, J=7.9 Hz, 1H), 7.86 (dt, J=2.0, 7.9 Hz, 2H), 7.35-7.31 (m, 1H), 7.22 (d, J=8.3 Hz, 2H), 6.99 (d, J=8.3 Hz, 2H), 3.65 (s, 2H), 2.45 (s, 3H), 2.21 (s, 3H) ppm. $^{13}$C NMR (CDCl$_3$) δ 155.7, 154.5, 153.8, 152.9, 149.5, 145.9, 139.7, 137.3, 137.2, 133.1, 130.7, 128.7, 124.2, 121.3, 118.5, 116.1, 110.0, 40.3, 13.6, 12.3 ppm.

Example 11

4-[5-Benzyl-3-(4-chloro-phenyl)-[1,2,4]triazol-1-yl]-6-pyridin-2-yl-[1,3,5]triazin-2-ylamine (Compound 133)

Step 1) Preparation of N-(4-Chloro-thiobenzoyl)-2-phenyl-acetamide

To a solution of 4-chlorothiobenzamide (0.519 g, 3.02 mmol) in acetone (5 mL) as added pyridine (0.367 mL, 4.53 mmol) and phenylacetyl chloride (0.480 mL, 3.63 mmol). The bright orange reaction mixture was heated to 55° C. for 1 hour. The reaction mixture was allowed to cool to room temperature, and water (20 mL) was added. The precipitate was removed by filtration, washed with water, and dried to provide 0.721 g (82%) of the product as a red solid: $^1$H NMR (CDCl$_3$) δ 9.34 (br s, 1H), 7.50-7.22 (m, 9H), 3.96 (s, 2H) ppm.

Step 2) Preparation of Compound 133

To a solution of N-(4-chloro-thiobenzoyl)-2-phenyl-acetamide (0.536 g, 1.85 mmol) and sodium acetate (ca. 0.25 g) in 1:1 acetic acid/1,4-dioxane (30 mL) was added 4-hydrazino-6-pyridin-2-yl-[1,3,5]triazin-2-ylamine (0.376 g, 1.85 mmol). The solution was heated to 90° C. and stirred for 15 hours. The reaction mixture was allowed to cool to room temperature, and water (100 mL) was added. The precipitate was removed by filtration, triturated with hot ethanol (300 mL), and dried to provide 0.489 g (60%) of the product as a white solid: $^1$H NMR (DMSO-d$_6$) δ 8.78 (d, J=4.3 Hz, 1H), 8.32 (d, J=6.1 Hz, 2H), 8.22 (d, J=7.8 Hz, 1H), 8.06 (d, J=8.5 Hz, 2H), 7.96 (dt, J=J=1.5, 7.8 Hz, 1H), 7.62-7.57 (m, 3H), 7.36-7.26 (m, 2H), 7.24-7.22 (m, 2H), 7.19-7.16 (m, 1H), 4.90 (s, 2H) ppm.

Example 12

2-[4-(4-Chloro-phenylsulfanyl)-3,5-dimethyl-pyrazol-1-yl]-4-pyridin-2-yl-[1,3,5]triazine (Compound 141)

Step 1) Preparation of 4-Pyridin-2-yl-[1,3,5]triazine-2-thiol

To a stirred solution of picolamide (1.50 g, 12.3 mmol) in N,N-dimethylformamide (20 mL) was added tert-butoxybis(dimethylamino)methane (5.2 mL, 25 mmol). The mixture was refluxed for 2.5 hours and then concentrated. The resulting viscous brown oil was taken up in a 0.5 M solution of sodium ethoxide in ethanol (50 mL, 25 mmol). Thiourea (0.72 g, 9.5 mmol) was added and the solution as refluxed for 2.5 hours. The reaction was concentrated and the residue partitioned between ethyl acetate and dilute aqueous sodium hydroxide solution. The aqueous layer was washed twice with ethyl acetate and neutralized with 1 N aqueous hydrochloric acid. The resulting precipitate was filtered off and rinsed with water. Vacuum oven dying afforded 0.72 g (40%) of crude product as a fine brown solid. This material was used without further purification in the next step.

Step 2) Preparation of 2-Methylsulfanyl-4-pyridin-2-yl-[1,3,5]triazine

To a stirred suspension of the product of step 1 (0.707 g, 3.72 mmol) in acetone (36 mL) was added sodium carbonate (0.79 g, 7.5 mmol) followed by iodomethane (0.35 mL, 5.6 mmol). After overnight stirring, the reaction was filtered free of undissolved solid and concentrated to afford product as light brown solid: $^1$H NMR (DMSO-d$_6$) δ 9.13 (s, 1H), 8.84-8.76 (m, 1H), 8.55-8.43 (m, 1H), 8.11-8.00 (m, 1H), 7.69-7.60 (m, 1H), 2.63 (s, 3H) ppm.

Step 3) Preparation of (4-Pyridin-2-yl-[1,3,5]triazin-2-yl)-hydrazine

A stirred solution of the product of step 2 (0.763 g, 3.74 mmol) and hydrazine hydrate (0.22 mL, 3.9 mmol) in ethanol (8 mL) was heated at reflux for 30 minutes. The reaction was cooled in an ice bath and the precipitate was filtered off. Vacuum oven drying afforded crude product as light brown solid. This material was used without further purification in the next step.

Step 4) Preparation of Compound 141

A stirred suspension of the product of step 3 (0.333 g, 1.77 mmol) and 3-(4-chloro-phenylsulfanyl)-pentane-2,4-dione (0.473 g, 1.95 mmol) in n-propanol was heated at 95° C. overnight. The reaction solution was concentrated directly onto silica and flash chromatographed (methylene chloride/methanol) to afford a dirty yellow solid. This material was further purified by trituration with diethyl ether to afford 0.056 g (8%) of product as a white solid: $^1$H NMR (DMSO-d$_6$) δ 9.44 (s, 1H), 8.94-8.77 (m, 1H), 8.68-8.43 (m, 1H), 8.18-7.96 (m, 1H), 7.77-7.57 (m, 1H), 7.45-7.24 (m, 2H), 7.20-6.98 (m, 2H), 2.83 (s, 3H), 2.20 (s, 3H) ppm.

Example 13

4-(4-Benzyl-3,5-dimethyl-pyrazol-1-yl)-6-pyridin-2-yl-[1,3,5]triazin-2-ylamine (Compound 142)

Step 1) Preparation of 3-Benzylpentane-2,4-dione

To a solution of sodium ethoxide (freshly prepared from sodium hydride (0.474 g, 19.8 mmol) and anhydrous ethanol (50 mL)) was added pentane-2,4-dione (6.00 g, 60.0 mmol). The resulting mixture was heated to 50° C. while a solution of benzyl bromide (3.42 g, 20 mmol) in ethanol (20 mL) was added over 30 minutes. The reaction was then heated to reflux. After 2 hours, the mixture was concentrated, and the residue was dissolved in ethyl acetate, washed three times with water, once with brine, dried (magnesium sulfate) and concentrated to afford an oil. Flash chromatography over silica (ethyl acetate/dichloromethane) afforded 3.13 g (82%) of a colorless oil. The proton spectrum showed the product exists as equal parts of the keto and enol tautomers: $^1$H NMR (CDCl$_3$) δ 16.81 (s, 0.5H), 7.13-7.32 (m, 5H), 4.00 (t, J=7.6 Hz, 0.5H), 3.65 (s, 1H), 3.14 (d, J=7.6 Hz, 0.5H), 2.06-2.13 (m, 6H) ppm.

Step 2) Preparation of Compound 142

A suspension of 4-hydrazino-6-pyridin-2-yl-[1,3,5]triazin-2-ylamine (5.25 g, 25.6 mmol), 3-benzylpentane-2,4-dione (5.0 g, 28.4 mmol), and p-toluenesulfonic acid monohydrate (0.475 g, 2.50 mmol) in dimethylsulfoxide (50 mL) was heated to 75° C. for 20 hours. The reaction mixture was allowed to cool to room temperature, and the suspension was dissolved in methylene chloride (700 mL). The solution was washed three times with water, once with brine, dried (magnesium sulfate), and concentrated to afford a moist solid. The crude product was suspended in ethyl acetate (50 mL), heated to reflux, allowed to cool to room temperature, and filtered (repeated three times). The final product was obtained as a white solid containing 3% dimethylsulfoxide by weight: 8.63 g (90%). $^1$H NMR (CDCl$_3$) δ 8.84-8.53 (m, 1H), 8.48 (d, J=7.9 Hz, 1H), 7.86-7.91 (m, 1H), 7.46-7.50 (m, 1H), 7.13-7.30 (m, 5H), 6.61 (br s, 1H), 6.40 (br s, 1H), 3.83 (s, 2H), 2.79 (s, 3H), 2.24 (s, 3H) ppm. MS (ESI) m/z 358 (M+H$^+$).

Example 14

4-[3,5-Dimethyl-4-(3-phenyl-propyl)-pyrazol-1-yl]-6-pyridin-2-yl-[1,3,5]triazin-2-lyamine (Compound 144)

Step 1) Preparation of 3-(3-Phenyl-propyl)-pentane-2,4-dione

A mixture of pentane-2,4-dione (3.87 g, 38.6 mmol), 3-phenyl-1-iodopropane (3.18 g, 12.9 mmol) and anhydrous potassium carbonate (1.7 g, 12.3 mmol) in acetone (7.5 mL) was heated to reflux for 24 hours. The room temperature reaction mixture was filtered, and the filter cake washed with acetone (25 mL×3). The combined filtrates were concentrated, and the residue was partitioned between ethyl acetate and water. The organic layer was washed with water and brine, dried (magnesium sulfate), and concentrated to an oil. Flash chromatography over silica (ethyl acetate/hexanes) afforded 1.13 g (42%) of a colorless oil. The proton spectrum in deuterochloroform showed the product exists as a mixture of keto and enol tautomers.

Step 2) Preparation of Compound 144

A solution of 4-hydrazino-6-pyridin-2-yl-[1,3,5]triazin-2-ylamine (6.17 g, 30.4 mmol), 3-(3-phenyl-propyl)-pentane-2,4-dione (6.66 g, 30.4 mmol), and p-toluenesulfonic acid monohydrate (0.05 g, 0.26 mmol) in dimethylsulfoxide (200 mL) was heated 75° C. for 18 hours. The solution was allowed to cool to room temperature then diluted with ethyl acetate (700 mL). The resulting solution was washed 3 times with water, once with brine, dried (magnesium sulfate) and concentrated to afford a cream colored solid. The solid was triturated in boiling ethyl acetate (200 mL), and the suspension allowed to cool to room temperature. After 2 hours, the product was collected by filtration and dried in vacuo to yield 5.87 g (50%) of a white solid: $^1$H NMR (CDCl$_3$) δ 8.84-8.54 (m, 1H), 8.49 (d, J=7.9 Hz, 1H), 7.87-7.91 (m, 1H), 7.46-7.50 (m, 1H), 7.18-7.32 (m, 5H), 6.44 (br s, 1H), 6.25 (br s, 1H), 2.73 (s, 3H), 2.65-2.73 (m, 2H), 2.44-2.49 (m, 2H), 2.31 (s, 3H), 1.79-1.86 (m, 2H) ppm. MS (ESI) m/z 386 (M+H$^+$).

Example 15

4-(4-Chloro-phenylsulfanyl)-5-methyl-2-(4-pyridin-2-yl-pyrimidin-2-yl)-2,4-dihydro-pyrazol-3-one (Compound 147)

Step 1) Preparation of 2-(4-Chloro-phenylsulfanyl)-3-oxo-butyric acid ethyl ester To a solution of ethyl 2-chloroacetoacetate (1.58 g, 9.61 mmol) in ethylene glycol dimethyl ether (30 mL) was added sodium hydrogencarbonate (ca. 15 g) and 4-chlorothiophenol (1.39 g, 9.61 mmol). The suspension was heated to reflux and stirred for 3 hours. The reaction mixture was allowed to cool to room temperature, and water (100 mL) was added. The mixture was extracted with ethyl ether (75 mL), and the organic extract was washed with brine (150 mL). The organic phase was dried (magnesium sulfate), filtered, and concentrated to afford a yellow oil. Flash chromatography over silica (ethyl acetate/hexanes) provided 1.44 g (55%) of the product as a colorless oil: $^1$H NMR (CDCl$_3$) δ 13.8 (s, 1H), 7.26-7.21 (m, 2H), 7.06-7.04 (m, 2H), 4.21 (q, J=7.1 Hz, 2H), 2.33 (s, 3H), 1.20 (t, J=7.1 Hz, 3H).

Step 2) Preparation of Compound 147

To a solution of 2-(4-chloro-phenylsulfanyl)-3-oxo-butyric acid ethyl ester (4.13 g, 15.1 mmol) in n-propanol (85 mL) was added (4-pyridin-2-yl-pyrimindin-2-yl)-hydrazine (2.84 g, 15.1 mmol) and p-toluenesulfonic acid monohydrate (ca. 25 mgs). The solution was heated to reflux and stirred for 15 hours. The reaction mixture was allowed to cool to room temperature, diluted with water (400 mL), and extracted with ethyl acetate (250 mL). The organic phase was washed water (200 mL) and brine (200 mL), dried (magnesium sulfate), filtered, and concentrated to afford a brown oil. The crude material was triturated with diethyl ether, and the solid that formed was isolated by filtration. Further trituration with a minimum amount of hot methanol provided the product as a tan solid. $^1$H NMR (CDCl$_3$) δ 12.8 (br s, 1H), 8.85 (d, J=5.3 Hz, 1H), 8.77 (d, J=4.3 Hz, 1H), 8.44 (d, J=7.8 Hz, 1H), 8.29 (d, J=5.3 Hz, 1H), 7.92 (dt, J=7.8 Hz, 1H), 7.51-7.48 (m, 1H), 7.19 (d, J=8.6 Hz, 2H), 7.09 (d, J=8.6 Hz, 2H), (s, 3H). $^{13}$C NMR (CDCl$_3$) δ 165.1, 159.1, 158.8, 157.1, 156.8, 152.0, 137.7, 136.6, 131.3, 129.2, 127.3, 126.8, 122.7, 114.6, 88.9, 13.3.

Example 16

2-[4-(4-Chloro-phenylsulfanyl)-5-methoxy-3-methyl-pyrazol-1-yl]-4-pyridin-2-yl-pyrimidine (Compound 148)

To a solution of 4-(4-chloro-phenylsulfanyl)-5-methyl-2 (4-pyridin-2yl-pyrimidin-2-yl)-2,4-dihydro-pyrazol-3-one (0.344 g, 0.869 mmol) in acetone (10 mL) was added potassium carbonate (ca. 3 g) and iodomethane (0.130 g, 0.912 mmol). The suspension was heated to reflux and stirred for 2 hours. The suspension was allowed to cool to room temperature, and water (100 mL) was added. The mixture was extracted with diethyl ether (50 mL), and the organic phase was washed with brine (50 mL), dried (magnesium sulfate), filtered and concentrated to afford a white solid. Flash chromatography over silica (methylene chloride/2M ammonia in methanol, two columns) provided 0.007 g (2%) of the product as a white solid. $^1$H NMR analysis was consistent with the assigned structure.

TABLE I
| Cpd No. | Method Used | R11 | R10 | R9 | R8 | R12 |
|---|---|---|---|---|---|---|
| 1 | 1 | 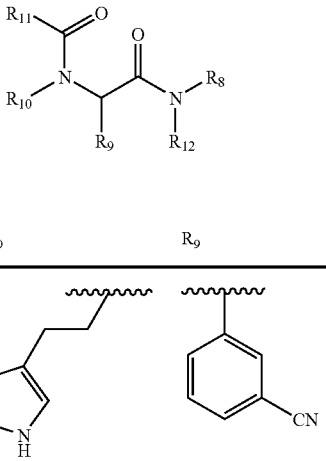 | 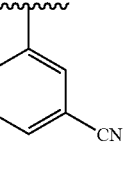 | 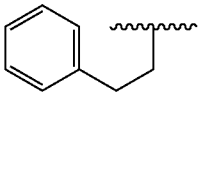 | 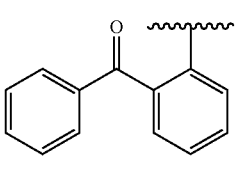 | H |
| 2 | 1 | 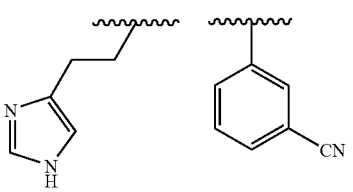 | 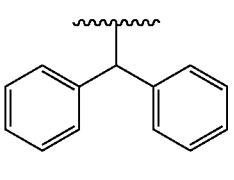 [SMILES: *C(c1ccccc1)c1ccccc1] | 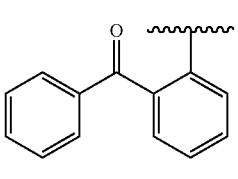 | 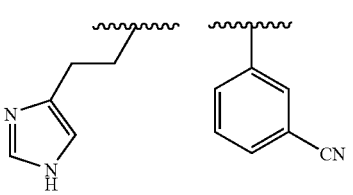 | H |
| 3 | 1 | 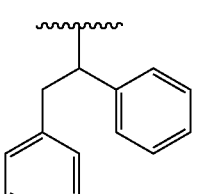 | 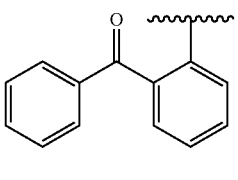 [SMILES: *c1ccccc1C(=O)c1ccccc1] | 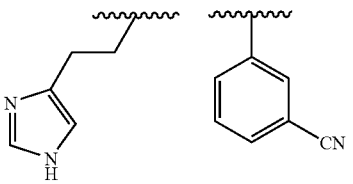 | 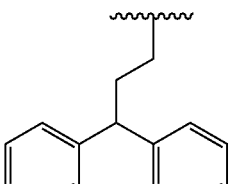 | H |
| 4 | 1 | 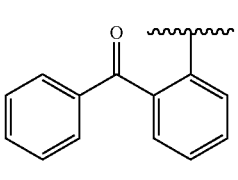 | | | 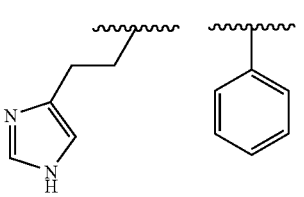 | H |
| 5 | 1 | 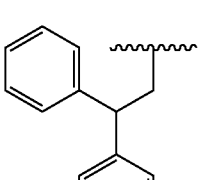 | | | 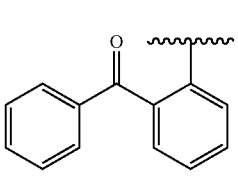 [SMILES: *c1ccccc1C(=O)c1ccccc1] | H |
| 6 | 1 | 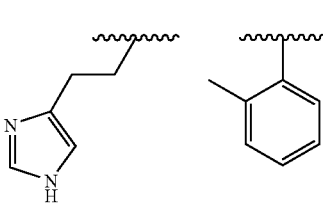 | | | 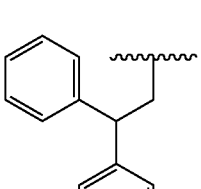 | H |

TABLE I-continued

| Cpd No. | Method Used | R11 | R10 | R9 | R8 | R12 |
|---|---|---|---|---|---|---|
| 7 | 1 | 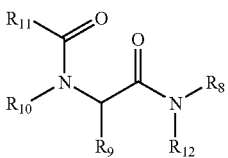 benzoyl-phenyl | 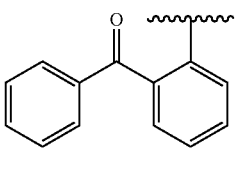 [SMILES: *c1ccccc1C(=O)c1ccccc1] imidazolylpropyl | 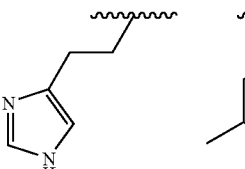 3-methylphenyl | 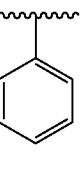 2,2-diphenylethyl | H |
| 8 | 1 | 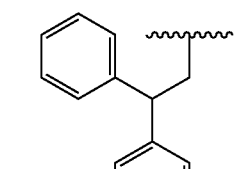 benzoyl-phenyl | 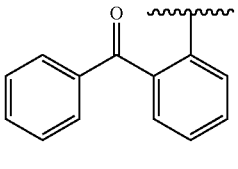 [SMILES: *c1ccccc1C(=O)c1ccccc1] imidazolylpropyl | 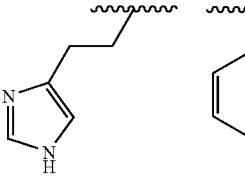 4-methylphenyl | 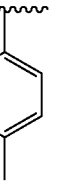 2,2-diphenylethyl | H |
| 9 | 1 | 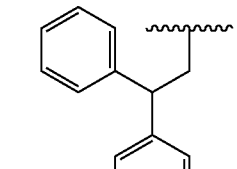 benzoyl-phenyl | 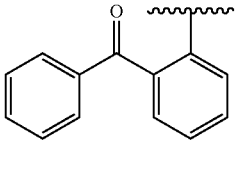 dimethylaminoethyl | 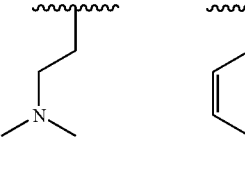 3-cyanophenyl | 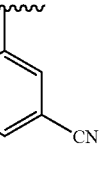 2,2-diphenylethyl | H |
| 10 | 1 | 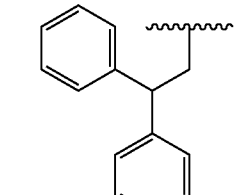 benzyl-phenyl | 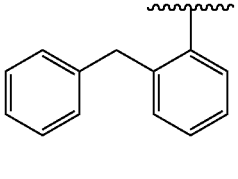 [SMILES: *c1ccccc1Cc1ccccc1] imidazolylpropyl | 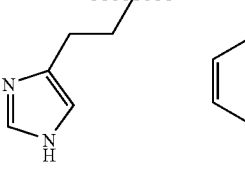 3-cyanophenyl | 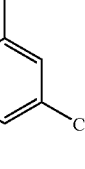 2,2-diphenylethyl | H |
| 11 | 1 | 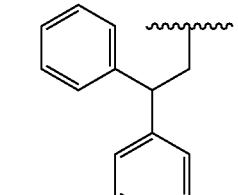 benzoyl-phenyl | 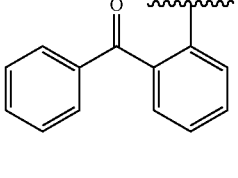 morpholinopropyl | 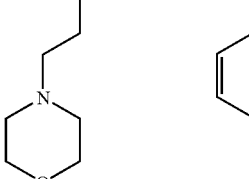 3-cyanophenyl | 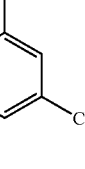 2,2-diphenylethyl | H |
| 12 | 1 | 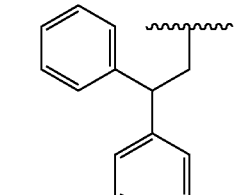 benzoyl-phenyl | 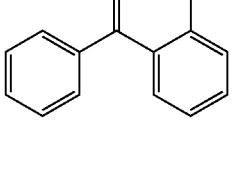 imidazolylpropyl | 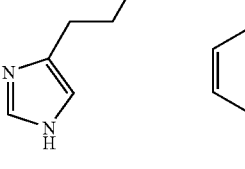 4-(methylthio)phenyl | 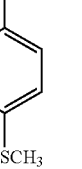 2,2-diphenylethyl | H |

TABLE I-continued

| Cpd No. | Method Used | $R_{11}$ | $R_{10}$ | $R_9$ | $R_8$ | $R_{12}$ |
|---|---|---|---|---|---|---|
| 13 | 1 | benzoyl (2-position) | 1-methylimidazol-4-yl-propyl | 3-cyanophenyl | 2,2-diphenylethyl | H |
| 14 | 1 | benzoyl (2-position) | 1-methylimidazol-5-yl-propyl | 3-cyanophenyl | 2,2-diphenylethyl | H |
| 15 | 1 | (pyridin-2-yl)carbonyl (2-position) | imidazol-4-yl-propyl | 3-cyanophenyl | 2,2-diphenylethyl | H |
| 16 | 1 | benzoyl (2-position) | imidazol-4-yl-propyl | 3-chlorophenyl | 2,2-diphenylethyl | H |
| 17 | 1 | benzoyl (2-position) | imidazol-4-yl-propyl | 3-trifluoromethylphenyl | 2,2-diphenylethyl | H |
| 18 | 1 | benzoyl (2-position) | imidazol-4-yl-propyl | 3-cyanophenyl | 2-(4-methoxyphenyl)ethyl | H |

TABLE I-continued
| Cpd No. | Method Used | R11 | R10 | R9 | R8 | R12 |
|---|---|---|---|---|---|---|
| 19 | 1 | 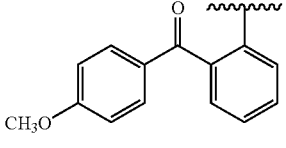 | 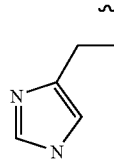 | 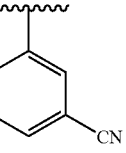 | 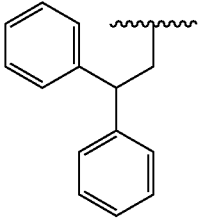 [SMILES: *CC(c1ccccc1)c1ccccc1] | H |
| 20 | 1 | 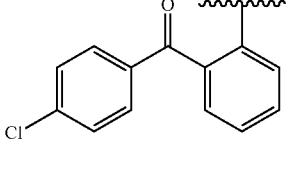 | 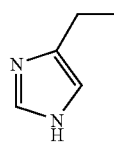 | 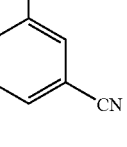 | 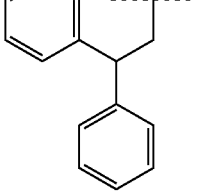 | H |
| 21 | 1 | 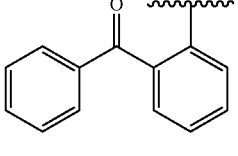 | 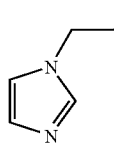 | 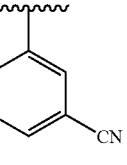 | 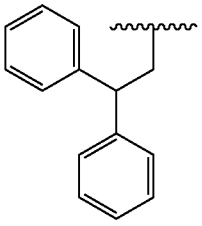 [SMILES: *CC(c1ccccc1)c1ccccc1] | H |
| 22 | 1 | 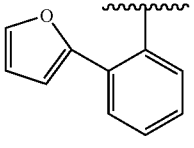 [SMILES: *c1ccccc1-c1ccco1] | 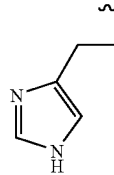 | 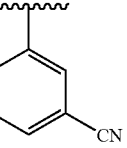 | 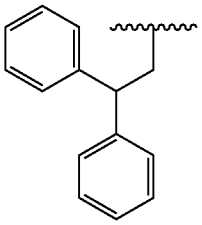 [SMILES: *CC(c1ccccc1)c1ccccc1] | H |
| 23 | 1 | 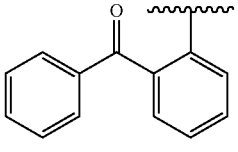 | 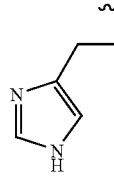 | 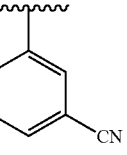 | 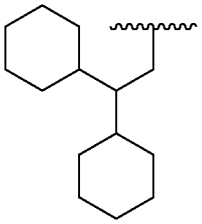 [SMILES: *CC(C1CCCCC1)C1CCCCC1] | H |
| 24 | 1 | 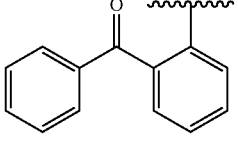 | 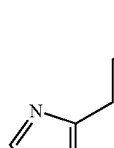 | 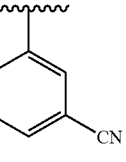 | 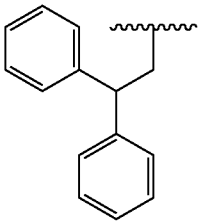 [SMILES: *CC(c1ccccc1)c1ccccc1] | H |

TABLE I-continued

| Cpd No. | Method Used | R11 | R10 | R9 | R8 | R12 |
|---|---|---|---|---|---|---|
| 25 | 1 | 2-benzoylphenyl | (1H-imidazol-4-yl)ethyl | 3-cyanophenyl | 2-cyclopentyl-2-phenylethyl | H |
| 26 | 4 | 2-benzoylphenyl | (1H-imidazol-4-yl)ethyl | phenyl | 2,2-diphenylethyl | CH3 |
| 27 | 1 | 2-benzoylphenyl | (1H-imidazol-4-yl)ethyl | 2-(trifluoromethyl)phenyl | 2,2-diphenylethyl | H |
| 28 | 1 | 2-benzoylphenyl | (1H-imidazol-4-yl)ethyl | 3-(trifluoromethyl)phenyl | 2,2-diphenylethyl | H |
| 29 | 1 | 2-(thiophen-2-yl)phenyl | (1H-imidazol-4-yl)ethyl | 3-cyanophenyl | 2,2-diphenylethyl | H |
| 30 | 1 | 2-benzoylphenyl | (1H-imidazol-4-yl)ethyl | 2-chlorophenyl | 2,2-diphenylethyl | H |

TABLE I-continued

| Cpd No. | Method Used | R11 | R10 | R9 | R8 | R12 |
|---|---|---|---|---|---|---|
| 31 | 1 | 2-benzoylphenyl | (1H-imidazol-4-yl)ethyl | 3-chlorobenzyl | 2,2-diphenylethyl | H |
| 32 | 1 | 2-benzoylphenyl | (1H-imidazol-4-yl)ethyl | 4-chlorobenzyl | 2,2-diphenylethyl | H |
| 33 | 1 | 2-benzoylphenyl | (1H-imidazol-4-yl)ethyl | 2-methoxybenzyl | 2,2-diphenylethyl | H |
| 34 | 1 | 2-benzoylphenyl | (1H-imidazol-4-yl)ethyl | 3-methoxybenzyl | 2,2-diphenylethyl | H |
| 35 | 1 | 2-benzoylphenyl | (1H-imidazol-4-yl)ethyl | 4-methoxybenzyl | 2,2-diphenylethyl | H |
| 36 | 1 | 2-benzoylphenyl | (1H-imidazol-4-yl)ethyl | 2-fluorobenzyl | 2,2-diphenylethyl | H |

TABLE I-continued

| Cpd No. | Method Used | R₁₁ | R₁₀ | R₉ | R₈ | R₁₂ |
|---|---|---|---|---|---|---|
| 37 | 1 | benzoyl-phenyl | imidazolyl-propyl | 3-fluorobenzyl | 2,2-diphenylethyl | H |
| 38 | 1 | benzoyl-phenyl | imidazolyl-propyl | 4-fluorobenzyl | 2,2-diphenylethyl | H |
| 39 | 1 | benzoyl-phenyl | imidazolyl-propyl | 3-cyanobenzyl | 2-phenyl-2-(pyridin-2-yl)ethyl | H |
| 40 | 1 | benzoyl-phenyl | imidazolyl-propyl | 3-azidobenzyl | 2,2-diphenylethyl | H |
| 41 | 1 | benzoyl-phenyl | 3-(dimethylamino)propyl | benzyl | 2,2-diphenylethyl | H |
| 42 | 1 | benzoyl-phenyl | imidazolyl-propyl | 3-methyl-4-methoxybenzyl | 2,2-diphenylethyl | H |

TABLE I-continued

| Cpd No. | Method Used | R11 | R10 | R9 | R8 | R12 |
|---|---|---|---|---|---|---|
| 43 | 1 | 2-benzoylphenyl | 2-(1H-imidazol-4-yl)ethyl | benzyl | 2,2-diphenylethyl | H |
| 44 | 1 | 2-benzoylphenyl | 2-(1H-imidazol-4-yl)ethyl | 3-cyanobenzyl | 2,2-diphenylethyl | H |
| 45[a] | 3 | 2-benzoylphenyl | 2-(1H-imidazol-4-yl)ethyl | phenyl | 2,2-diphenylethyl | H |
| 46[a] | 3 | 2-benzoylphenyl | 2-(1H-imidazol-4-yl)ethyl | phenyl | 2,2-diphenylethyl | H |
| 47[b] | 3 | 2-benzoylphenyl | 2-(1H-imidazol-4-yl)ethyl | benzyl | 2,2-diphenylethyl | H |
| 48[b] | 3 | 2-benzoylphenyl | 2-(1H-imidazol-4-yl)ethyl | benzyl | 2,2-diphenylethyl | H |

TABLE I-continued

| Cpd No. | Method Used | R₁₁ | R₁₀ | R₉ | R₈ | R₁₂ |
|---|---|---|---|---|---|---|
| 49ᶜ | 1 | 2-benzoylphenyl | imidazol-4-yl-propyl | 3-cyanophenyl | 2,2-diphenylethyl | H |
| 50ᶜ | 1 | 2-benzoylphenyl | imidazol-4-yl-propyl | 3-cyanophenyl | 2,2-diphenylethyl | H |
| 51 | 2 | 2-benzoylphenyl | imidazol-4-yl-propyl | 4-cyanophenyl | 2,2-diphenylethyl | H |
| 52 | 2 | 2-benzoylphenyl | imidazol-4-yl-propyl | 5-phenylfuran-2-yl | 2,2-diphenylethyl | H |
| 53 | 2 | 2-(phenoxymethyl)phenyl | imidazol-4-yl-propyl | 3-cyanophenyl | 2,2-diphenylethyl | H |
| 54 | 2 | 2-(pivaloyl)phenyl | imidazol-4-yl-propyl | 3-cyanophenyl | 2,2-diphenylethyl | H |

TABLE I-continued
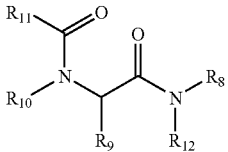
| Cpd No. | Method Used | R11 | R10 | R9 | R8 | R12 |
|---|---|---|---|---|---|---|
| 55 | 2 | 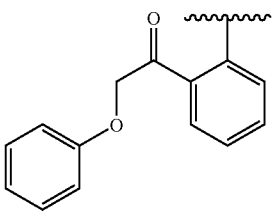 [SMILES: *c1ccccc1C(=O)COc1ccccc1] | 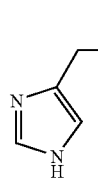 | 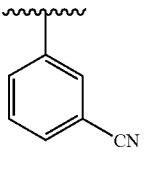 [SMILES: *c1cccc(C#N)c1] | 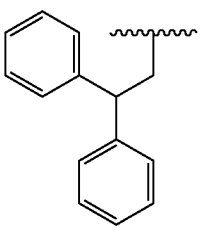 [SMILES: *CC(c1ccccc1)c1ccccc1] | H |
| 56 | 2 | 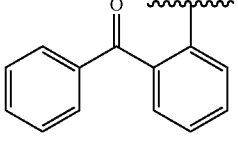 | 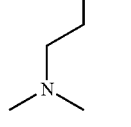 | 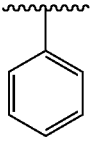 | 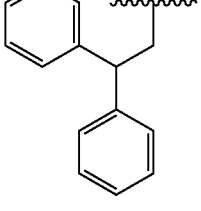 | H |
| 57 | 2 | 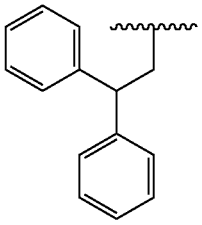 | 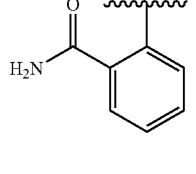 | 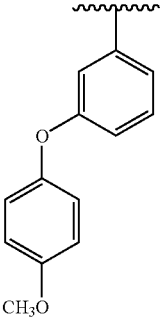 | 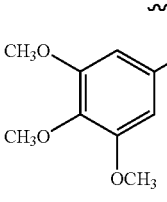 | H |
| 58 | 2 | 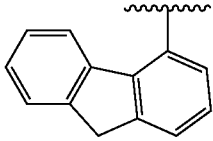 | 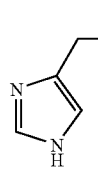 | 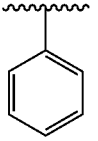 | 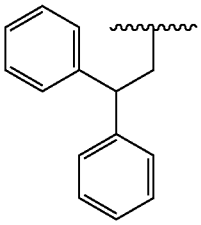 [SMILES: *CC(c1ccccc1)c1ccccc1] | H |
| 59 | 2 | 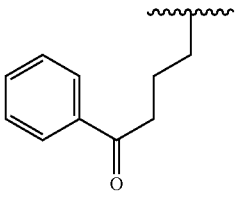 [SMILES: *CCCC(=O)c1ccccc1] | 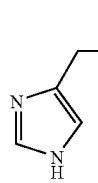 | H, H | 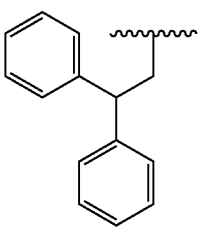 [SMILES: *CC(c1ccccc1)c1ccccc1] | H |

TABLE I-continued
| Cpd No. | Method Used | R11 | R10 | R9 | R8 | R12 |
|---|---|---|---|---|---|---|
| 60 | 2 | 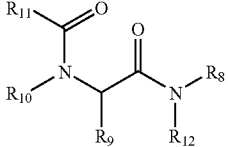 | 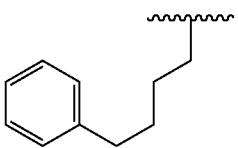 [SMILES: *CCCCc1ccccc1] | 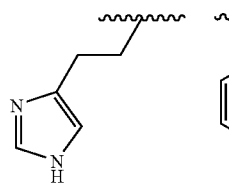 | 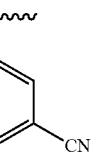 | H |
| 61 | 2 | 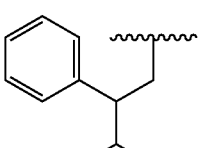 | 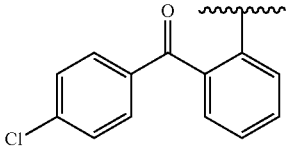 [SMILES: *c1ccccc1C(=O)c1ccc(Cl)cc1] | 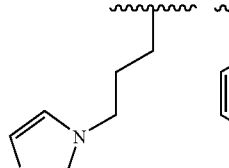 | 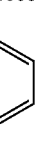 | H |
| 62 | 2 | 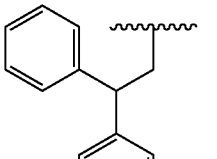 | 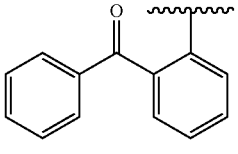 [SMILES: *c1ccccc1C(=O)c1ccccc1] | 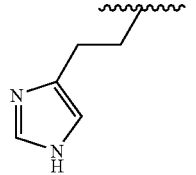 [SMILES: *CCc1c[nH]cn1] | 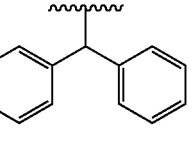 | H |
| 63 | 2 | 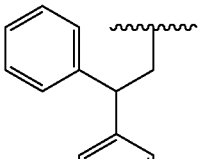 | 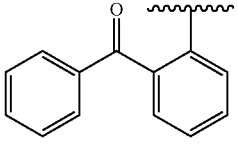 [SMILES: *c1ccccc1C(=O)c1ccccc1] | 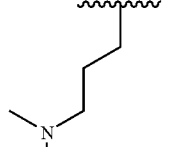 | 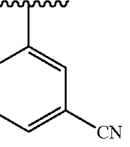 | H |
| 64 | 2 | 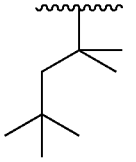 [SMILES: *C(C)(C)CC(C)(C)C] | 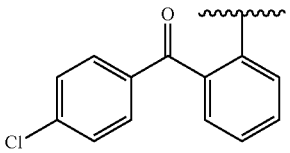 [SMILES: *c1ccccc1C(=O)c1ccc(Cl)cc1] | 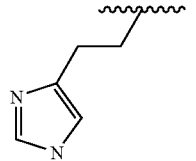 | 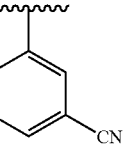 | H |
| 65 | 2 | 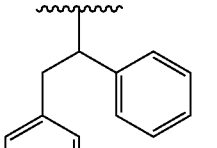 | 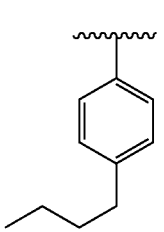 [SMILES: *c1ccc(CCCC)cc1] | 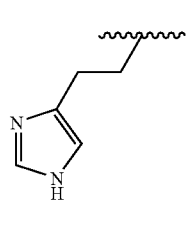 [SMILES: *CCc1c[nH]cn1] | 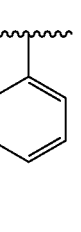 | H |

TABLE I-continued

| Cpd No. | Method Used | R₁₁ | R₁₀ | R₉ | R₈ | R₁₂ |
|---------|-------------|-----|-----|-----|-----|-----|
| 66 | 2 | 2,3-dimethoxyphenyl | (imidazol-4-yl)propyl | 3-cyanophenyl | 3,3-diphenylpropyl | H |
| 67 | 2 | (naphthalen-2-yl)methyl | (imidazol-4-yl)propyl | 3-cyanophenyl | 3,3-diphenylpropyl | H |
| 68 | 2 | naphthalen-1-yl | (imidazol-4-yl)propyl | 3-cyanophenyl | 3,3-diphenylpropyl | H |
| 69 | 2 | 2-cyclohexylethyl | (imidazol-4-yl)propyl | 3-cyanophenyl | 3,3-diphenylpropyl | H |
| 70 | 2 | 3-methoxyphenyl | (imidazol-4-yl)propyl | 3-cyanophenyl | 3,3-diphenylpropyl | H |
| 71 | 2 | 1-methylpyrrol-2-yl | (imidazol-4-yl)propyl | 3-cyanophenyl | 2-(4-methoxyphenyl)ethyl | H |

TABLE I-continued

| Cpd No. | Method Used | $R_{11}$ | $R_{10}$ | $R_9$ | $R_8$ | $R_{12}$ |
|---|---|---|---|---|---|---|
| 72 | 2 | cyclopentylethyl | imidazol-4-ylethyl | 3-cyanophenyl | 4-methoxyphenylethyl | H |
| 73 | 2 | 4-oxopentyl | imidazol-4-ylethyl | 3-cyanophenyl | 4-methoxyphenylethyl | H |
| 74 | 2 | quinoxalin-2-yl | imidazol-4-ylethyl | 3-cyanophenyl | 4-methoxyphenylethyl | H |
| 75 | 2 | (2-methyl-1H-indol-3-yl)ethyl | imidazol-4-ylethyl | 3-cyanophenyl | 4-methoxyphenylethyl | H |
| 76 | 2 | 3-(1H-indol-3-yl)propyl | imidazol-4-ylethyl | 3-cyanophenyl | 4-methoxyphenylethyl | H |
| 77 | 2 | (1H-indol-3-yl)methyl | imidazol-4-ylethyl | 3-cyanophenyl | 4-methoxyphenylethyl | H |

TABLE I-continued

| Cpd No. | Method Used | R11 | R10 | R9 | R8 | R12 |
|---|---|---|---|---|---|---|
| 78 | 2 | 5-bromoindol-3-ylmethyl | (1H-imidazol-4-yl)ethyl | 3-cyanophenyl | 4-methoxyphenethyl | H |
| 79 | 2 | 3-chlorophenyl | (1H-imidazol-4-yl)ethyl | 3-cyanophenyl | 4-methoxyphenethyl | H |
| 80 | 2 | quinoxalin-2-yl | (1H-imidazol-4-yl)ethyl | 3-cyanophenyl | 2,2-diphenylethyl | H |
| 81 | 2 | 3-amino-1H-pyrazol-4-yl | (1H-imidazol-4-yl)ethyl | 3-cyanophenyl | 2,2-diphenylethyl | H |
| 82 | 2 | 2-hydroxy-3-(1H-indol-3-yl)propyl | (1H-imidazol-4-yl)ethyl | 3-cyanophenyl | 2,2-diphenylethyl | H |
| 83 | 2 | 3-fluorophenyl | (1H-imidazol-4-yl)ethyl | 3-cyanophenyl | 2,2-diphenylethyl | H |

TABLE I-continued

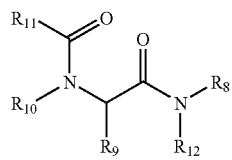

| Cpd No. | Method Used | R11 | R10 | R9 | R8 | R12 |
|---|---|---|---|---|---|---|
| 84 | 2 | 3-(indol-3-yl)propyl | (1H-imidazol-4-yl)ethyl | 3-cyanophenyl | 2,2-diphenylethyl | H |
| 85 | 2 | (5-bromo-1H-indol-3-yl)methyl | (1H-imidazol-4-yl)ethyl | 3-cyanophenyl | 2,2-diphenylethyl | H |
| 86 | 2 | 3-methoxyphenyl | (1H-imidazol-4-yl)ethyl | 3-cyanophenyl | 2,2-diphenylethyl | H |
| 87 | 2 | hydroxy(phenyl)methyl | (1H-imidazol-4-yl)ethyl | 3-cyanophenyl | diphenylmethyl | H |
| 88 | 2 | biphenyl-2-yl | (1H-imidazol-4-yl)ethyl | 3-cyanophenyl | diphenylmethyl | H |
| 89 | 2 | 2-benzoylphenyl | (1H-imidazol-4-yl)ethyl | 3-cyanophenyl | diphenylmethyl | H |

TABLE I-continued

| Cpd No. | Method Used | R11 | R10 | R9 | R8 | R12 |
|---|---|---|---|---|---|---|
| 90 | 2 | 2-thienyl | (imidazol-4-yl)ethyl | 3-cyanophenyl | diphenylmethyl | H |
| 91 | 2 | 2-(4-chlorobenzoyl)phenyl | (imidazol-4-yl)ethyl | 3-cyanophenyl | 3,3-diphenylpropyl | H |
| 92 | 2 | isobutyl | (imidazol-4-yl)ethyl | 3-cyanophenyl | 2-(4-methoxyphenyl)ethyl | H |

[a] Compound 45 was prepared at the (R)-enantiomer. Compound 46 was prepared as the (S)-enantiomer. Enantiomeric excesses were determined to be 91.4% and 91.8% respectively.

[b] Compound 47 was prepared at the (R)-enantiomer. Compound 48 was prepared as the (S)-enantiomer. Enantiomeric excesses were determined to be 100% (within detection limits) and >95% respectively.

[c] Compounds 49 and 50 are the (−) and (+) enantiomers, respectively, of compound 44. Preparative chiral HPLC was used for the resolution (ChiralPack OD, 2 × 25 cm; eluant: 40/60 carbon dioxide/acetonitrile; detection 260 nM).

TABLE II

| Cpd No. | Ex. No. | R19 | R4 | R3 | n | X | W | V |
|---|---|---|---|---|---|---|---|---|
| 93 | 6 | H | H | $CH_3$ | 0 | O | N | CH |
| 94 | 6 | 4-Cl | H | $CH_3$ | 0 | O | N | CH |
| 95 | 6 | 4-F | H | $CH_3$ | 0 | O | N | CH |
| 96 | 6 | 4-$CH_3$O | H | $CH_3$ | 0 | O | N | CH |
| 97 | 6 | 4-$(CH_3)_2$CH | H | $CH_3$ | 0 | O | N | CH |
| 98 | 6 | 4-$CF_3$ | H | $CH_3$ | 0 | O | N | CH |
| 99 | 6 | 4-$CF_3$O | H | $CH_3$ | 0 | O | N | CH |

TABLE II-continued

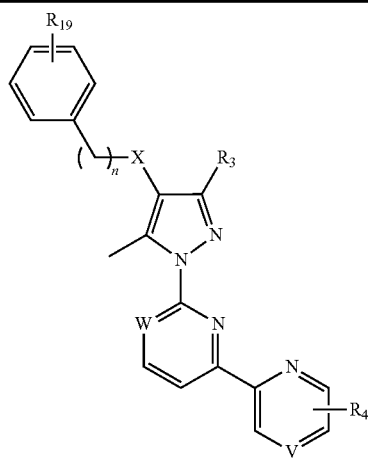

| Cpd No. | Ex. No. | R19 | R4 | R3 | n | X | W | V |
|---|---|---|---|---|---|---|---|---|
| 100 | 7 | 4-(CH3OH) | H | CH3 | 0 | O | N | CH |
| 101 | 7 | 4-CHO | H | CH3 | 0 | O | N | CH |
| 102 | 7 | 4-(N-morpholino)CH2 | H | CH3 | 0 | O | N | CH |
| 103 | 7 | 4-(N-tetrahydroisoquinolino)CH2 | H | CH3 | 0 | O | N | CH |
| 104 | 7 | 4-(4-Benzyl-piperazin-1-yl)CH2 | H | CH3 | 0 | O | N | CH |
| 105 | 7 | 4-(4-(2-fluoro-phenyl)piperazin-1-yl)CH2 | H | CH3 | 0 | O | N | CH |
| 106 | 6 | 4-Cl | H | CH3 | 0 | O | N | N |
| 107 | 6 | 4-Cl | H | CH3 | 1 | O | N | CH |
| 108 | 8 | H | H | CH3 | 0 | S | N | CH |
| 109 | 8 | 2-Cl | H | CH3 | 0 | S | N | CH |
| 110 | 8 | 3-Cl | H | CH3 | 0 | S | N | CH |
| 111 | 8 | 4-Cl | H | CH3 | 0 | S | N | CH |
| 112 | 8 | 4-F | H | CH3 | 0 | S | N | CH |
| 113 | 8 | 4-CH3O | H | CH3 | 0 | S | N | CH |
| 114 | 8 | 3,4-diCl | H | CH3 | 0 | S | N | CH |
| 115 | 8 | 4-Cl | 4-CH3 | CH3 | 0 | S | N | CH |
| 116 | 8 | 4-Cl | 5-CH3 | CH3 | 0 | S | N | CH |
| 117 | 8 | H | H | CH3 | 1 | S | N | CH |
| 118 | 8 | 2-Cl | H | CH3 | 1 | S | N | CH |
| 119 | 8 | 4-Cl | H | CH3 | 1 | S | N | CH |
| 120 | 8 | 4-F | H | CH3 | 1 | S | N | CH |
| 121 | 8 | 4-CH3 | H | CH3 | 1 | S | N | CH |
| 122 | 8 | 4-CH3O | H | CH3 | 1 | S | N | CH |
| 123 | 8 | 4-CF3O | H | CH3 | 1 | S | N | CH |
| 124 | 9 | 4-Cl | H | CH3 | 1 | SO2 | N | CH |
| 125 | 10 | 4-Cl | H | CH3 | 0 | O | C | CH |
| 126 | 10 | 4-Cl | H | CH3 | 1 | S | C | CH |
| 147 | 15 | 4-Cl | H | OH | 0 | S | N | CH |
| 148 | 16 | 4-Cl | H | OCH3 | 0 | S | N | CH |

TABLE III

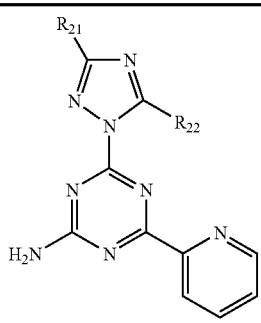

| Cmp No. | Methhod Used | R21 | R22 |
|---|---|---|---|
| 127 | 11 | 2,4-diClPh | 4-ClPhCH2 |
| 128 | 11 | 2,4-diFPh | 4-ClPhCH2 |

TABLE III-continued

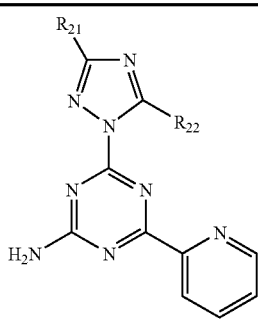

| Cmp No. | Methhod Used | R21 | R22 |
|---|---|---|---|
| 129 | 11 | 4-t-BuPh | 4-ClPhCH2 |
| 130 | 11 | 4-ClPh | 4-ClPhCH2 |

TABLE III-continued

| Cmp No. | Methhod Used | R21 | R22 |
|---|---|---|---|
| 131 | 11 | 2,4-diFPh | 4-(CH3O)PhCH2 |
| 132 | 11 | 4-ClPh | 3-(CH3O)PhCH2 |
| 133 | 11 | 4-ClPh | PhCH2 |
| 134 | 11 | 4-ClPh | c-C6H11 |
| 135 | 11 | 4-ClPh | c-(C5H9)CH2CH2 |
| 136 | 11 | 4-ClPh | c-C5H9 |
| 137 | 11 | 4-ClPh | (CH3)3CCH2 |
| 138 | 11 | 4-ClPh | 3,4-di(CH3O)PhCH2 |

TABLE IV

| Cpd No. | Method Used | R23 | R24 | n | X |
|---|---|---|---|---|---|
| 139 | 8 | 4-Cl | NH2 | 0 | S |
| 140 | 9 | 4-Cl | NH2 | 0 | SO2 |
| 141 | 12 | 4-Cl | H | 0 | S |
| 142 | 13 | H | NH2 | 0 | C |
| 143 | 13 | 4-Cl | NH2 | 1 | C |
| 144 | 14 | H | NH2 | 2 | C |
| 145 | 13 | 4-Cl | NH2 | 1 | C |
| 146 | 14 | H | NH2 | 2 | C |

II. Biological Results

Example 17

In Vitro Activity of Compounds in TNF-α and VCAM Assays

Description of Table V: The results shown in Table V were obtained using the TNF-α assays performed as described in the protocols entitled "Method for TNF High Throughput Screen" and "Method for VCAM High Throughput Screen", which are detailed below. These assays measure a cellular response to TNF-α stimulation, and the data published in the table are expressed as percentage inhibitions. Percentage inhibition is computed on a scale of 0 to 100% where 0 percent inhibition means the compound has no effect in the assay (the response is indistinguishable from TNF-α treatment alone), and 100% inhibition means that when the compound is present at the stated concentration, the response in the assay is the same as if TNF-α were not added. These two assays measure two different outcomes of TNF-α treatment, cell death and Vascular Cell Adhesion Molecule (VCAM) expression, and capture two of TNF-α's many biological effects. TNF-α induced apoptosis is a mechanism by which TNF-α production during immune/inflammatory responses can lead to direct cellular and tissue damage. TNF-α VCAM expression in endothelial cells is a response that allows leukocytes to leave the blood and enter a site of immune/inflammatory response. Both of these activities could lead to pathology in immune/inflammatory diseases. In the first column of the table, the percentage inhibition of the TNF-α driven apoptosis assay when the compounds are tested at 1 µM concentration is presented. The second column in the table lists the IC50 for the compound, a standard measure using a dilution series in the assay, and fitting a siginoidal curve to the resulting dose-response curve. The IC50 is the concentration (derived analytically from the siginoidal function) at which the compound would inhibit 50% of the response in the assay. The third and fourth column list the corresponding analysis for the TNF-α driven VCAM assay. In Table VI, data corresponding to the data in column 1 of Table V is shown, with human cells replacing the mouse cells used in the high throughput screen. It will be understood that the table demonstrates that a class of compounds can have its best activity in one assay or the other, or that there can be crossover such that the compounds can have activity to some degree in both assays. While not being bound by theory, we believe this data shows that the compounds can have a modulating effect in more than one activity. As a consequence, the compounds will have use in treating more than one TNF-α mediated condition, and may be selected according to the manner in which the condition manifests. This corresponds to the use of these compounds in the treatment of human disease.

TNF High Throughput Screen.
Protocol:
1. Plate $4 \times 10^4$ L929 cells in 100 µl of complete EMEM in Costar 96 well plates in PM.
2. The next day, pretreat with compound, inhibitor and control vehicle for 2 hours.
3. After 2 hours pretreatment, add 10 µl 5 ng/ml human TNF-α and actinomycin D (40 µg/ml final concentration).
4. Incubate overnight.
5. In AM, remove supernatant.
6. Wash on a plate washer (0.9% NaCl).
7. Add 100 µl Crystal Violet 0.1% in 20% ETOH.
8. Incubate at RT for 10 minutes.
9. Wash on plate washer.
10. Air dry wells at 37° C.
11. Add 100 µl of methanol to each well.
12. Shake plates on orbital shaker and read at 595 nm on plate reader.

VCAM High Throughput Screen:
Protocol:
1. Plate Primary human umbilical vein endothelial cellsat $1.8 \times 10^4$ cells/well in a 96-well tissue culture plate.
2. Return Plates to 37° C. incubator for 48-72 hours before assay.
3. On assay day, aspirate wells and add 180 µL of endothelial growth cell medium (EGM) to each well.

4. Add Compound to each well.
5. Shake plates for 3 minutes.
6. Incubate plate for 1 hour at 37° C.
7. Add Tumor Necrosis Factor (TNF) at 1.0 ng/ml final concentration.
8. Shake plates for 3 minutes.
9. Incubate plate for 2 hours at 37° C.
10. Remove plate from incubator and wash plate 3 times with phosphate buffered saline (PBS) using a plate washer.
11. Add anti-VCAM antibody at 0.5 μg/ml final concentration.
12. Incubate at 4° C. overnight.
13. Wash 3 times with PBS on plate washer.
14. Add goat anti-mouse horseradish peroxidase conjugate.
15. Incubate at room temperature for one hour.
16. Wash 3 times with PBS on plate washer.
17. Add TMB to each well for 15 minutes at room temperature.
18. Stop reaction with 100 μL of 2 N sulfuric acid.
19. Read absorbance at 450 nm.

TABLE V

In Vitro Activity of Compounds in TNF-α and VCAM Assays

| Cpd. No. | TNFα % Inh. @ 1 μM | TNFα IC$_{50}$ (μM) | VCAM % Inh. @12.5 μM | VCAM IC$_{50}$ (μM) |
|---|---|---|---|---|
| 1 | | 2.64 | | |
| 2 | | 5.65 | | |
| 3 | | 1.29 | | |
| 4 | | 0.941 | | |
| 5 | | 0.872 | | |
| 6 | | 1.06 | | |
| 7 | | 4.01 | | |
| 8 | | 1.62 | | |
| 9 | | 0.496 | | |
| 10 | | 3.68 | | |
| 11 | | 2.89 | | |
| 12 | | 5.15 | | |
| 13 | | 1.37 | | |
| 14 | | 1.79 | | |
| 15 | | 0.386 | | |
| 16 | | 1.32 | | |
| 17 | | 1.5 | | |
| 18 | | 2.68 | | |
| 19 | | 0.457 | | |
| 20 | | 0.299 | | |
| 21 | | 0.913 | | |
| 22 | | 3.85 | | |
| 23 | | 2.58 | | |
| 24 | | 1.03 | | |
| 25 | | 1.58 | | |
| 26 | | 3.36 | | |
| 27 | | 2.72 | | |
| 28 | | 5.27 | | |
| 29 | | 3.72 | | |
| 30 | | 2.36 | | |
| 31 | | 3.35 | | |
| 32 | | 2.33 | | |
| 33 | | 2.35 | | |
| 34 | | 1.54 | | |
| 35 | | 2.64 | | |
| 36 | | 2.15 | | |
| 37 | | 2.36 | | |
| 38 | | 2.79 | | |
| 39 | | 1.32 | | |
| 40 | | 1.74 | | |
| 41 | | 6.49 | | |
| 42 | | 0.779 | 16 | |
| 43 | | 2.98 | | |
| 44 | | 0.41 | 24.4 | |
| 45 | | 3.34 | | |
| 46 | | 4.37 | | |
| 47 | | 5.58 | | |
| 48 | | 4.05 | | |
| 49 | | 1.53 | | |
| 50 | | 0.39 | | |
| 51 | | 3.56 | | |
| 52 | | 3.49 | | |
| 53 | | 7.13 | | |
| 54 | | 6.03 | | |
| 55 | | 7.64 | | |
| 56 | | 6.63 | | |
| 57 | 56 | | | |
| 58 | 50 | | | |
| 59 | 51 | | | |
| 60 | 50 | | | |
| 61 | 51 | | | |
| 62 | 59 | | | |
| 63 | 55 | | | |
| 64 | 63 | | | |
| 65 | 52 | | | |
| 66 | 51 | | | |
| 67 | 52 | | | |
| 68 | 57 | | | |
| 69 | 61 | | | |
| 70 | 58 | | | |
| 71 | 57 | | | |
| 72 | 57 | | | |
| 73 | 76 | | | |
| 74 | 55 | | | |
| 75 | 67 | | | |
| 76 | 56 | | | |
| 77 | 54 | | | |
| 78 | 60 | | | |
| 79 | 62 | | | |
| 80 | 53 | | | |
| 81 | 50 | | | |
| 82 | 55 | | | |
| 83 | 56 | | | |
| 84 | 52 | | | |
| 85 | 52 | | | |
| 86 | 53 | | | |
| 87 | 50 | | | |
| 88 | 53 | | | |
| 89 | 56 | | | |
| 90 | 51 | | | |
| 91 | 71 | | | |
| 92 | 52 | | | |
| 93 | | | 1.21 | |
| 94 | | | 0.029 | |
| 95 | | | 0.2 | |
| 96 | | | 0.046 | |
| 97 | | | 0.397 | |
| 98 | | | 0.058 | |
| 99 | | | 0.177 | |
| 100 | | | 3.46 | |
| 101 | | | 17.9 | |
| 102 | | | 0.431 | |
| 103 | | | 0.709 | |
| 104 | | | 0.05 | |
| 105 | | | 0.089 | |
| 106 | | | 0.96 | |
| 107 | | | | 47 |
| 108 | | | 2.28 | |
| 109 | | | 0.63 | |
| 110 | | | 6.34 | |
| 111 | | | 0.132 | |
| 112 | | | 0.309 | |
| 113 | | | 0.498 | |
| 114 | | | 1.44 | |
| 115 | | | 19.4 | |
| 116 | | | 355 | |
| 117 | | | | 16 |
| 118 | | | | 72 |
| 119 | | | | 7.95 |
| 120 | | | | 13.2 |

TABLE V-continued

In Vitro Activity of Compounds in TNF-α and VCAM Assays

| Cpd. No. | TNFα % Inh. @ 1 μM | TNFα IC$_{50}$ (μM) | VCAM % Inh. @12.5 μM | VCAM IC$_{50}$ (μM) |
|---|---|---|---|---|
| 121 | | | | 9.93 |
| 122 | | | | 11.9 |
| 123 | | | | 7.1 |
| 124 | | | | 13.4 |
| 125 | | 0.023 | | |
| 126 | | 37.9 | | 2.52 |
| 127 | | 2.2 | | |
| 128 | | 20.6 | | 8.67 |
| 129 | | 19.5 | | |
| 130 | | 8.96 | | |
| 131 | | 12.8 | | |
| 132 | | 1.39 | | |
| 133 | | 19.5 | | |
| 134 | | 0.526 | | |
| 135 | | 0.275 | | |
| 136 | | 1.44 | | |
| 137 | | 9.67 | | |
| 138 | 54[a] | | | |
| 139 | 62[b] | | | |
| 140 | | 1.77 | | |
| 141 | | 0.0011 | | |
| 142 | | 0.152 | | |
| 143 | | 6.06 | | |
| 144 | | 0.015 | | |
| 145 | | 2.5 | | |
| 146 | | 0.197 | | |
| 147 | | 0.734 | | |
| 148 | | 32.1 | | |

[a]Inhibition measured at 2 μM
[b]Inhibition measured at 25 μM

TABLE VI

Compound 44 can inhibit the TNF-α induced apoptosis in primary human fibroblasts

| | OD 595 nm | Standard Deviation | % Rescue |
|---|---|---|---|
| DMSO | 0.189 | 0.005 | N/A |
| TNF + DMSO | 0.091 | 0.006 | N/A |
| 2 μM Compound 44 | 0.109 | 0.008 | 18.4 |
| 4 μM Compound 44 | 0.147 | 0.033 | 57.1 |
| 8 μM Compound 44 | 0.198 | 0.002 | 109.2 |

Normal human dermal fibroblasts were seeded into 96-well plates at $3 \times 10^4$ cells/well. Cells were pretreated for 2 hours with 2 μg/ml Actinomycin D and either Compound 44 or DMSO as a vehicle control. Cells were then exposed to 2 μg/ml TNF-α for 24 hours and stained with crystal violet/ethanol. Crystal violet was solubilized with methanol and absorbance at 595 nm was read on a microtiter plate reader.

Example 18

In Vivo Activity of Compounds in Sepsis and IBD Models and Pharmacokinetic Parameters Sepsis Model:

Sepsis was induced in the C57/BL mouse by the intravenous injection of 20 ng of lipopolysaccharide/animal plus 20 mgs d-galactosamine/animal. Inhibition was measured as the prevention of mortality over a three day period. Compounds were administered intraperitoneally in 10% cremophore/10% ethanol/80% normal saline one hour before induction.

Inflammatory Bowel Disease Model:

Groups of three male rats weighing 150±10 g and fasted for 24 hours were used. Distal colitis was induced by intracolonic instillation of 0.5 ml/rat DNBS (2,4-dinitrobenzene sulfonic acid, 60 mg/ml in ethanol 30%) after which air (2 ml) was gently injected through the cannula to ensure that the solution remains in the colon. A test compound was administered orally 24 and 2 hours before DNBS-instillation and then daily for 5 days in a total of 7 doses. The animals were sacrificed 24 hours after the final dose of test compound administration and each colon was removed and weighed.

TABLE VII

In Vivo Activity of Compounds in Sepsis and IBD Models and Pharmacokinetic Parameters

| | Sepsis: Murine LPS-d-galactosamine model # % inhibition | Inflammatory Bowel Disease: Rat DNBS model* % inhibition of colonic weight gain | Pharmacokinetic Parameters | |
|---|---|---|---|---|
| | | | $t^{1/2}$ | % oral bioavailability |
| 44 | 33 +/− 1 @ 200 mg/kg (2 exp.) | 44 +/− 8 @ 100 mg/kg (2 exp.) | 2.3 | 26 |
| 119 | 33 @ 200 mg/kg | 51% @ 100 mg/kg | 2.3 | Undetectable |
| 94 | Not active below 200 mg/kg | 18% @ 20 mg/kg | 10.9 | Undetectable |
| 43 | 33 @ 10 mg/kg | 31% @ 50 mg/kg | 3.6 | <1 |

Example 19

In Vivo Activity of Compounds in Experimental Allergic Encephalitis (Murine Model of Multiple Sclerosis)

SJL mouse strain were immunized subcutaneously with proteolipid peptide amino acid residues 139-151 in Complete Freund's Adjuvant. Pertussis toxin was injected intravenously on day 1 and 3 post-induction. Weight loss occurred at day 7 post-immunization with paralysis ensuing between days 9 and 14 post-immunization.

TABLE VIII

In Vivo Activity of Compounds in Experimental Allergic Encephalitis (Murine Model of Multiple Sclerosis)

| Compound | Dosing regimen[1] | Ratio of activity disease severity score (ADSS)[4] at last day of dosing for treated vs. control | % inhibition of disease[5] | % Survival[7] of treated vs. % survival of controls |
|---|---|---|---|---|
| 44 Induction regimen | 15 mgs/kg/day/i.p.[2] from day 1–21 | 1.9/3.35 | 44.0% $p^6 = 0.06$ | 75 vs. 50 |
|  | 75 mgs/kg/day/i.p. from day 1–21 | 0.8/3.35 | 75.7% $p = 0.001$ | 100 vs. 50 |
| 44 Therapeutic regimen | 15 mgs/kg/day/i.p. from day 7–21 | 2.6/4.6 | 43.5% $p = 0.08$ | 70 vs. 11 |
|  | 75 mgs/kg/day/i.p. from day 7–21 | 1.1/4.6 | 76.1% $p = 0.001$ | 100 vs. 11 |
| 44 Oral therapeutic regimen | 75 mgs/kg/day/i.p. from day 7–28 | 2.2/4.4 | 50% $p = 0.002$ | 89 vs 20 |
| 94 Induction Regimen | 75 mgs/kg/day/i.p. from day 1–18 | 2.15/3.53 | 39.1% $p^6 = 0.045$ | 80 vs 67 |

[1]Compounds solublized in 10% cremophore and 10% ethanol 80% normal saline.
[2]Compounds administered intraperitoneally.
[3]Compound administered orally.
[4]ADSS is activity disease severity score where >1 is significant disease. Paralysis starts at the tail and progresses towards head of the mouse where a limp tail is a 1 and a complete paralysis is a 5. Animals are euthanized at greater than or equal to a score of 4.
[5]% inhibition of ADSS = (average test ADSS - average control ADSS/control) × 100.
[6]P values calculated using Student's T Test.
[7]Survival indicates those animals remaining post-euthanasia.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating TNF-α mediated inflammation in a patient in need of such treatment, comprising administering to the patient a therapeutically effective amount of a compound of Formula III,

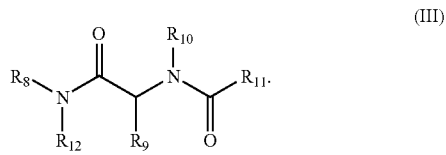

(III)

or a physiologically acceptable salt thereof, wherein:
$R_8$ is an unsubstituted alkyl; an alkyl group substituted with one or more groups selected from fluoro, chloro, bromo, iodo, nitro, hydroxyl, —$NR_{13}R_{14}$, —$C(O)R_{15}$, cyano and cycloalkyl; a substituted or unsubstituted aryl; an aralkyl substituted in the aromatic portion of the aralkyl; a heteroaralkyl substituted in the heteroaryl portion of the heteroaralkyl; an aralkyl or heteroaralkyl substituted in the alkyl portion of the aralkyl or heteroaralkyl with one or more groups selected from fluoro, chloro, bromo, iodo, nitro, hydroxyl, —$NR_{13}R_{14}$, —$C(O)R_{15}$, cyano and cycloalkyl; or an unsubstituted aralkyl or heteroaralkyl;
$R_9$ is a substituted or unsubstituted aryl, a substituted or unsubstituted aralkyl, a substituted or unsubstituted heteroaryl or a substituted or unsubstituted heteroaralkyl;
$R_{10}$ is alkyl substituted with $NR_{13}R_{14}$, a substituted or unsubstituted aryl, a substituted or unsubstituted heteroaralkyl, or a substituted or unsubstituted heterocycloalkylalkyl;
$R_{11}$ is a substituted or unsubstituted alkyl, a substituted or unsubstituted aryl, a substituted or unsubstituted aralkyl, a substituted or unsubstituted heteroaryl, a substituted or unsubstituted heteroaralkyl, a substituted or unsubstituted benzophenonyl, or a substituted or unsubstituted cycloalkylalkyl;
$R_{12}$ is —H;
$NR_{13}R_{14}$ is a heterocycloalkyl, and
$R_{15}$ is —H, an alkyl, an aryl or an aralkyl.

2. The method of claim 1, wherein the compound is represented by the following structural formula:

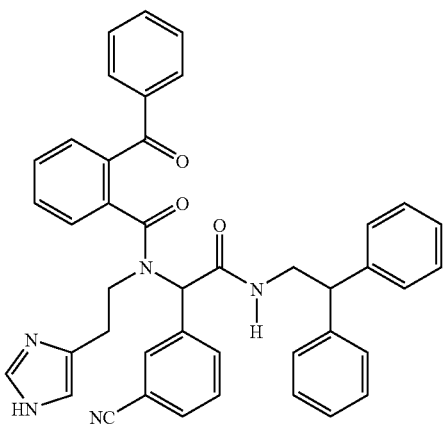

or a physiologically acceptable salt thereof.

3. The method of claim 1, wherein $R_8$ is substituted or unsubstituted phenyl, phenyl-$C_1$-$C_4$-alkyl, diphenyl-$C_1$-$C_4$- alkyl, linear $C_1$-$C_{12}$-alkyl, branched $C_1$-$C_{12}$-alkyl, cyclic $C_3$-$C_{12}$-alkyl, or dicycloalkyl-$C_1$-$C_4$-alkyl.

4. The method of claim 3, wherein $R_8$ is phenyl, phenyl-$C_1$-$C_4$-alkyl, or diphenyl-$C_1$-$C_4$-alkyl wherein the phenyl group or phenyl groups optionally bear one or more substituents independently selected from the group consisting of $C_1$-$C_4$-alkoxy, $C_1$-$C_4$-alkyl and cyano.

5. The method of claim 4, wherein the phenyl group or phenyl groups bear one or more substituents independently selected from the group consisting of methoxy, methyl, ethyl and cyano.

6. The method of claim 1, wherein $R_8$ is selected from the group consisting of 2,2-diphenylethyl, 2-(4-ethylphenyl)ethyl, benzyl, diphenylmethyl, 1,2-diphenylethyl, 3,3-diphenylpropyl, 3,4,5-trimethoxybenzyl, 2,4,4-trimethylisopentyl, 2-(4-methoxyphenyl)ethyl, 2-cyclopentyl-2-phenylethyl, or 2-phenyl-2-pyridylethyl.

7. The method of claim 1, wherein $R_9$ is substituted or unsubstituted phenyl, substituted or unsubstituted phenyl-$C_1$-$C_4$-alkyl, diphenyl-$C_1$-$C_4$-alkyl, phenylfuranyl or heteroaryl-$C_1$-$C_4$-alkyl.

8. The method of claim 7, wherein $R_9$ is phenyl, phenyl-$C_1$-$C_4$-alkyl, diphenyl-$C_1$-$C_4$-alkyl wherein the phenyl group or phenyl groups bear one or more substituents independently selected from the group consisting of cyano, $C_1$-$C_4$-alkyl-S—, a halogen, a halogenated $C_1$-$C_4$-alkyl, $C_1$-$C_4$-alkoxy, trifluoromethyl, and substituted and unsubstituted phenoxy.

9. The method of claim 7, wherein $R_9$ is phenyl, phenyl-$C_1$-$C_4$-alkyl, diphenyl-$C_1$-$C_4$-alkyl wherein the phenyl group or phenyl groups bear one or more substituents independently selected from the group consisting of cyano, methyl, methoxy, phenoxy, chloro-substituted phenoxy, methoxy-substituted phenoxy and methyl-substituted phenoxy.

10. The method of claim 1, wherein $R_9$ is phenyl, 2-cyanophenyl, 3-cyanophenyl, 4-cyanophenyl, diphenylmethyl, pyrazolylmethyl, 2,4-dimethylphenyl, 2-methylphenyl, 3-methylphenyl, 4-methylphenyl, 2-methyl-4-methoxyphenyl, 3-methyl-4-methoxyphenyl, 4-methylthiophenyl, 3-chlorophenyl, 3-trifluoromethylphenyl, benzyl, 2-trifluoromethylbenzyl, 3-trifluoromethylbenzyl, 2-chlorobenzyl, 3-chlorobenzyl, 4-chlorobenzyl, 2-methoxybenzyl, 3-methoxybenzyl, 4-methoxybenzyl, 2-fluorobenzyl, 3-fluorobenzyl, 4-fluorobenzyl, 3-azidylphenyl, 3-(4-methoxyphenoxy)phenyl, or 5-phenylfuran-2-yl.

11. The method of claim 1, wherein $R_{10}$ is substituted or unsubstituted phenyl, unsubstituted heteroaraalkyl group, unsubstituted heterocycloalkylalkyl group, or an alkyl substituted with —$NR_{13}R_{14}$.

12. The method of claim 11, wherein $R_{10}$ is 2-(imidazol-4-yl)ethyl, 3-(imidazol-4-yl)propyl, 3-(imidazol-1-yl)propyl, 2-(3-methylimidazol-4-yl)ethyl, 2-(morpholin-4-yl)ethyl, 2-(4-pyrazolyl)ethyl, 4-pyrazolylmethyl, 2-N,N-dimethylaminoethyl, 3-N,N-dimethylaminopropyl, or 2-(aminocarbonyl)phenyl.

13. The method of claim 1, wherein $R_{11}$ is a linear or branched $C_1$-$C_4$-alkyl, substituted or unsubstituted phenyl, substituted or unsubstituted benzophenonyl, pyrazolyl, aminopyrazolyl, substituted or unsubstituted indolyl-$C_1$-$C_4$-alkyl, thiophenyl, quinoxaline, substituted or unsubstituted phenyl-$C_1$-$C_4$-alkyl, pyridylcarbonylphenyl, phenylcarbonyl-$C_1$-$C_4$-alkyl, naphthyl, naphthyl-$C_1$-$C_4$-alkyl, diphenyl-$C_1$-$C_4$-alkyl, $C_5$-$C_8$-cycloalkyl-$C_1$-$C_4$-alkyl, $C_1$-$C_4$-alkylcarbonyl-$C_1$-$C_4$-alkyl, fluorenyl, pyrrolyl, N-methylpyrrolyl, or pyridyl.

14. The method of claim 13, wherein $R_{11}$ is a phenyl, phenyl-$C_1$-$C_4$-alkyl, phenylcarbonyl-$C_1$-$C_4$-alkyl, naphthyl-$C_1$-$C_4$-alkyl, diphenyl-$C_1$-$C_4$-alkyl, $C_5$-$C_8$-cycloalkyl-$C_1$-$C_4$-alkyl, fluorenyl or pyridyl substituted with one or more substituents independently selected from $C_1$-$C_4$-alkyl and $C_1$-$C_4$-alkoxy.

15. The method of claim 13, wherein $R_{11}$ is a benzophenonyl group, wherein said benzophenonyl group is substituted with a $C_1$-$C_4$-alkoxy group, a $C_1$-$C_4$-alkyl group or a chlorine atom.

16. The method of claim 1, wherein $R_{11}$ is benzophenon-2-yl, 4'-methoxybenzophenon-2-yl, 4'-chlorobenzophenon-2-yl, 2-(furan-2-yl)phenyl, 2-(thiophen-2-yl)phenyl, 2-benzylphenyl, 2-pyridylcarbonylphenyl, 2-(phenoxymethyl)phenyl, 2-(t-butylcarbonyl)phenyl, 2,2-diphenylethyl, 1-fluorenyl, (naphth-2-yl)methyl, naphth-1-yl, 3-(phenylcarbonyl)propyl, 4-phenylbutyl, 4-butylphenyl, 2-(4-chlorophenylcarbonyl)phenyl, 3-methoxyphenyl, N-methylpyrrol-2-yl, 2,3-dimethoxyphenyl, 3-butyl-2-pyridyl, 2-naphthylmethyl, 2-cyclohexylethyl, 3-methoxyphenyl, N-methyl-2-pyrrolyl, 2-cyclopentylethyl, 3-oxobutyl, 2-benzopyrazyl, quinoxalin-2-yl, 3-idolyl, (2-methylindol-3-yl)methyl, 3-(indol-3-yl)propyl, (indol-3-yl)methyl, (5-bromoindol-3-yl)methyl, 3-chlorophenyl, 3-aminopyrazol-4-yl, 2-(indol-3-yl)-1-hydroxyethyl, 3-fluorophenyl, 1-phenyl-1-hydroxymethyl, 2-phenylphenyl, 2-phenoxyphenyl, thiophen-2-yl, or isopropyl.

* * * * *

UNITED STATES PATENT AND TRADEMARK OFFICE
CERTIFICATE OF CORRECTION

PATENT NO.         : 8,518,999 B2                                Page 1 of 1
APPLICATION NO.    : 11/292325
DATED              : August 27, 2013
INVENTOR(S)        : Scott F. Sneddon et al.

It is certified that error appears in the above-identified patent and that said Letters Patent is hereby corrected as shown below:

On the title page, item (54) and in the specification, column 1, in the title, delete

"MODULATORS OF TNF-αSIGNALING"

and insert

-- MODULATORS OF TNF-α SIGNALING --

Signed and Sealed this
Fourth Day of March, 2014

Michelle K. Lee
*Deputy Director of the United States Patent and Trademark Office*